United States Patent [19]
Grieco et al.

[11] Patent Number: 5,965,493
[45] Date of Patent: *Oct. 12, 1999

[54] THERAPEUTIC QUASSINOID PREPARATIONS WITH ANTINEOPLASTIC, ANTIVIRAL, AND HERBISTATIC ACTIVITY

[75] Inventors: Paul A. Grieco, Gosport; D. James Morre, West Lafayette, both of Ind.; Thomas H. Corbett, Gross Pointe Park; Frederick A. Valeriote, Utica, both of Mich.

[73] Assignees: Advanced Research and Technology Institute, Inc., Bloomington, Ind.; The Board of Governors of Wayne State University, Detroit, Mich.; Purdue Reseach Foundation, West Lafayette, Ind.

[*] Notice: This patent is subject to a terminal disclaimer.

[21] Appl. No.: 08/836,805

[22] PCT Filed: Nov. 3, 1995

[86] PCT No.: PCT/US95/14321

§ 371 Date: May 1, 1997

§ 102(e) Date: May 1, 1997

[87] PCT Pub. No.: WO96/14065

PCT Pub. Date: May 17, 1996

Related U.S. Application Data

[63] Continuation-in-part of application No. 08/334,735, Nov. 4, 1994, Pat. No. 5,639,712.
[51] Int. Cl.⁶ .................................................. A01N 43/12
[52] U.S. Cl. .......................... 504/297; 549/275; 514/453
[58] Field of Search .......................... 504/297; 549/275; 514/453

[56] References Cited

PUBLICATIONS

CA103:178479 Jun. 1985.
CA106:98111 Sep. 1986.
Cassady et al., "Anticancer Agents Based on Natural Procut Models", published 1980 by Academic Press (New York, New York) Jan. 1980.
Waterman et al., "The Chemistry and Chemical Taxonomy of the Rutales <" published 1983 by Academic Press (London) Jan. 1983.
Kupchan et al. J. Med. Chem. vol. 19(9) pp. 1130–33 Feb. 1976.
Grieco et al. Phytochem. vol. 37(5) pp. 1451–54 Apr. 1994.
Pierre et al. Biochem. Biophys. Res. Comm. vol. 93(3) pp. 675–686 Apr. 1980.
Geissman, T. A., *New Substances of Plant Origin*, Ann. Rev. Pharmaol., 1964, pp. 305–316.
Nyburg, S. C., Walford, G. L., Yates, P., *The Configuration of Glaucarubin*, Chem. Commun., 1965, p. 203.
Connolly, J. D., Overton, K. H., *The Chemistry and Biochemistry of the Limonoids and Quassinoids*, Progess in Phytochemistry, 1970.
Polonsky, Judith, *Quassinoids Bitter Principles*, Forschr. Chem. Org. Naturst., 1973, pp. 101–150.
Kupchan, S. M., Lacadie, J. A., Howie, G. A., Sickles, B.R., *Structural Requirements for Biological Activity among Antileukemic Glaucarubolone Ester Quassinoids*, J. Med. Chem., 1976, pp. 1130–1133.
Wall, M.E., Wani, M.C., *Antineoplastic Agents from Plants*, Ann. Rev. Pharmacol, Toxicol., 1977, pp. 117–132.
Seida, Ahmed, et al. *Potential Anticancer Agents IX.*, Lloydia, 1978, pp. 584–587.
Pierre, Alain, et al., *Structural Requirements of Quassinoids For the Inhibition of Cell Transformation*, Biochem. Biophys. Res. Commun. 1980, pp. 675–686.
Suffness, M. And Douros J., *Drugs of Plant Orgin*, Methods Cancer Research, 1979, 73–126.
Cassady, J. M. Douros, J.D., *Anticancer Agents Based on National Product Models*, Academic Press, 1980, pp. 254–269.
Polonsky, Judith, *Chemistry and Biological Activity of the Quassinoids*, The Chemistry and Biological Activity of the Quassinoids, The Chemistry and Chemical Taxonomy of the Rutales, Academic Press, Inc., 1983, pp. 247–266.
Polonsky, Judith, *Quassinoid Bitter Principles II*, Fortschr. Chem. Org. Naturst., 1985, pp. 221–264.
O'Neill, Melanie J., et al., *Plants as Sources of Antimalarial Drugs: In Vitro Antimalarial Activities of Some Quassinoids*, Antimicrob. Ag. Chemother., 1986, 101–104.
Lidert, Zev, Wing, Keith, *Insect Antifeedant and Growth Inhibitory Activity of Forty–Six Quassinoids on Two Species of Agricultural Pests*, Journal of Natural Products, 1987, pp. 442–448.
Corbett, Thomas H. And Valeriote Frederick A., edited by Kallman, PhD, Robert E., *Rodent Tumor Models in Experimental Cancer Therapy*, Pergamon Press, pp. 233–247 1987.
Grieco, Paul et al., Total Synthesis of the Highly Oxygenated Quassinoid, Journal of American Chemical Society, 1989 pp. 6287–6294.
Valeriote, Frederick et al., Valeriote, Frederick et al., *Cytotoxic anticancer Drugs: Models and Concepts for Drug Discovery and Development*, Kluwer Academic Publishers, 1990, 1–87.
Collins, Grieco and Gross, Synthetic Studies on Quassinoids: Total Synthesis of +)–Shinjulactone C, Journal of Organic Chemistry, 1990.

(List continued on next page.)

*Primary Examiner*—Brian M. Burn
*Attorney, Agent, or Firm*—Leydig, Voit & Mayer, Ltd.

[57] ABSTRACT

The present invention includes purified and isolated quassinoids and synthetically derived quassinoid analogs based on a picrasane carbon skeleton. Novel sidechains at C-15 incorporating water solubilizing agents such as glycine are discussed. Therapeutic methods taking advantage of anticancer, antiviral, and herbistatic properties of these quassinoids are disclosed, including use against solid tumors and human immunodeficiency virus infected cells.

42 Claims, 11 Drawing Sheets

OTHER PUBLICATIONS

Grieco, Collins, Moher, Fleck and Gross, Synthetic Studies on Quassinoids: Total Synthesis of Chaparrinone, Glaucarubolone and Glaucarubinone, Journal of American Chemical Society, 1993, 6078–83.

Grieco, Moher, Sey, Huffman and Grieco, Quassinoids Peninsularinone and a Steroid From Casatela Peninsularis, Phytochemistry, vol. 37, pp. 1451–1454, 1994.

van Dang, Rode, Stuppner, Quantitative electronic structure-–activity relationship (QESAR) of natural cytotoxic compounds: European Journal of Pharmaceutical Sciences, 1994, 331–350.

Suntory, Ltd. Abstract of JP 60–104093, Jun. 1985.

Yamazaki et al. Abstract of JP 61–200901, Sep. 1986.

Cassady et al., *Anticancer Agents Based on Natural Product Models,* Academic Press pp. 254–269, 1980.

Kupchan et al., "Structural Requirements for Biological Activity Among Antileukemic Claucarubolone Ester Quassinoids" J. Of Medicinal Chemistry 19(9): 1130–1133 1976.

Grieco et al., "A Quassinoid (Peninsularinone) and a Steroid from Castela peninsularis"*Phytochemistry*, 37(5): 1451–1454 1993.

Pierre et al., "Structural Requirements of Quassinoids for the Inhibition of Cell Transformation". Biochemical and Biophysical Research Communications. 93(3): 675–686 (1980).

THERAPEUTIC QUASSINOID PREPARATIONS WITH ANTINEOPLASTIC, ANTIVIRAL, AND HERBISTATIC ACTIVITY

This application is a continuation-in-part of U.S. patent application Ser. No. 08/334,735 filed Nov. 4, 1994, now U.S. Pat. No. 5,639,712.

This invention was made with United States government support under National Institutes of Health grant numbers CA 22865 and CA 46560. The United States government has certain rights in the invention.

BACKGROUND AND SUMMARY OF THE INVENTION

The botanical family Simaroubaceae includes numerous species distributed primarily in pantropical regions. These plant species have been the source of a large family of bitter terpenoid substances collectively termed quassinoids. Like many plant alkaloids or naturally isolated plant extracts, quassinoids have been found to have diverse biologic activity, including anti-malarial, anti-insecticidal, anti-amoebicidal, anti-leukemic, and anti-viral activity.

The great majority of quassinoids are heavily oxygenated lactones that include the following twenty carbon skeleton,

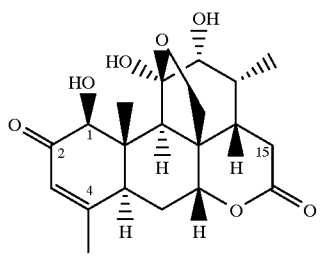

(Formula I)

conventionally termed picrasane, although eighteen, nineteen, and twenty-five carbon skeletons are also known. Many variant ring structures and sidechains, particularly at C-15, are known (See eg. Polonsky, "Quassinoid Bitter Principles II", Fortschr.Chem.Org Naturst, Progress in the Chemistry of Organic Natural Products, 1985, 47, 221). The present invention includes both novel and synthetically derived quassinoid analogs, as well as novel uses for such synthetic quassinoids and previously identified and isolated natural quassinoids. In one aspect of the present invention, disclosed is a compound characterized by the formula

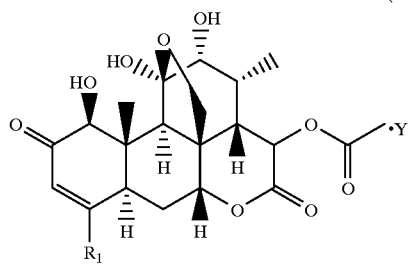

(Formula II)

wherein $R_1$ represents hydrogen, oxygen, alkyl, alkenyl, acyl, aryl, halogen, sulfo, nitro, carboxyl, hydroxyl, hydroxyalkyl, alkoxy, or other water soluble sidechain, and Y is a sidechain comprising hydrogen, alkyl, hydroxyalkyl, carboxyl, aryl, alkenyl, cycloalkanes, cycloalkenes, glycosaccharides, water soluble sidechains, amino acid, peptide, and any of the foregoing attached at C-15 by an ether, ester, carbonyl, or glycosidic linkage.

In preferred embodiments, the sidechain Y is represented by the formula

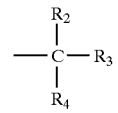

(Formula III)

wherein $R_2$, $R_3$, and $R_4$ taken separately or together represent hydrogen, alkyl, hydroxyalkyl, carboxyl, aryl, alkenyl, cycloalkanes, cycloalkenes, glycine, glycosaccharides, water soluble sidechains, amino acids, peptide, and any of the foregoing attached to the central carbon by an ether, ester, carbonyl, or glycosidic linkage.

Specific embodiments of the present invention include those wherein $R_2$ is a methyl group, $R_3$ is a methyl group, and $R_4$ is a hydroxyl group, those wherein $R_2$ is a methyl group, $R_3$ is a methyl group, and $R_4$ is a hydroxyalkane, hydroxyalkene, glycyl, glycosaccharides, or water soluble sidechain, or those wherein $R_2$ is an ethyl group, $R_3$ is a hydroxyl group, and $R_4$ is an ethyl group. In addition, compounds wherein $R_2$ is a methyl group, $R_3$ is a methyl group, and $R_4$ is a hydroxymethyl group, or wherein $R_2$ is a methyl group, $R_3$ is a methyl group, and $R_4$ is a methyl group are included in the scope of the present invention.

Alternatively, the Y sidechain of Formula III above can be modified to support ring structures such as aryls or cycloalkanes. For example, $R_2$ and $R_3$ taken together can form a $C_3$ to $C_8$ membered carbon ring, and $R_4$ substituted with a hydroxymethyl group. More specifically, $R_2$ and $R_3$ can be taken together form a three membered cycloalkane, with $R_4$ being a hydroxymethyl group.

In still other embodiments, the sidechain Y can be represented as

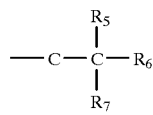

(Formula IV)

wherein $R_5$, $R_6$, and $R_7$ taken separately or together represent hydrogen, alkyl, hydroxyalkyl, carboxyl, aryl, alkenyl, cycloalkanes, cycloalkenes, glycine, glycosaccharides, or water soluble sidechains, amino acids, peptide, and any of the foregoing attached to the terminal carbon by an ether, ester, carbonyl, or glycosidic linkage.

More specifically, embodiments of the present invention wherein $R_5$ is an isopropyl group, $R_6$ is an isopropyl group, and $R_7$ is a hydroxyl group; wherein $R_5$ and $R_6$ taken together comprise a double bonded carbon group, and $R_7$ is a methyl group; or wherein $R_5$ is a hydrogen, $R_6$ is a hydrogen, and $R_7$ is a carboxyl group are contemplated as within the scope of the present invention.

In addition, cyclic ring structures wherein $R_5$ and $R_6$ taken together form a $C_3$ to $C_8$ membered carbon ring, and $R_7$ further comprises hydrogen, alkyl, hydroxyalkyl, carboxyl, aryl, alkenyl, cycloalkanes, cycloalkenes, glycine, glycosaccharides, water soluble sidechains, amino acids, peptide, and any of the foregoing attached to the terminal $R_7$ carbon by an ether, ester, carbonyl, or glycosidic linkage are within the scope of the present invention. More specifically, those embodiments wherein $R_5$ and $R_6$ taken together form a four membered cycloalkane, and $R_7$ is a hydroxyl group; wherein $R_5$ and $R_6$ taken together form a five membered cycloalkane, and $R_7$ is a hydroxyl group; wherein $R_5$ and $R_6$ taken together form a six membered cycloalkane, and $R_7$ is a hydroxyl group; wherein $R_5$ and $R_6$ taken together form a seven membered cycloalkane, and $R_7$ is a hydroxyl group; wherein $R_5$ and $R_6$ taken together form a four membered cycloalkane, and $R_7$ comprises a group having the formula

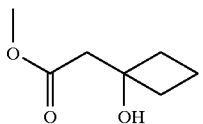

(Formula V)

are considered to be within the scope of this invention.

Still other embodiments of the present invention also include the compound of formula IV above, wherein $R_5$ and $R_6$ taken together comprise a double bonded carbon group, and together with $R_7$ form a five membered cycloalkene. Alternatively, the sidechain Y of the compound represented by Formula II can be represented as

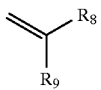

(Formula VI)

wherein $R_8$ and $R_9$ taken separately or together represent hydrogen, alkyl, hydroxyalkyl, carboxyl, aryl, alkenyl, cycloalkanes, cycloalkenes, glycine, glycosaccharides, water soluble sidechains, amino acids, peptide, and any of the foregoing attached to the terminal carbon by an ether, ester, carbonyl, or glycosidic linkage. More specifically, those embodiments of the present invention wherein $R_8$ is a methyl group and $R_9$ is a methyl group; or wherein $R_8$ is an isopropyl group and $R_9$ is an isopropyl group are within the scope of the present invention.

Another aspect of the present invention is the use of the foregoing described synthetically derived quassinoids, or previously known, purified and isolated quassinoids, for the treatment in conjunction with suitable pharmaceutical carriers of neoplastic disorders such as solid tumors. For example, a chemotherapeutic composition for treatment of cancer can comprise a combination of a compound characterized by the formula

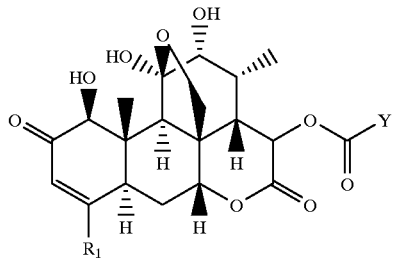

(Formula VII)

wherein $R_1$ represents hydrogen, oxygen, alkyl, alkenyl, acyl, aryl, halogen, sulfo, nitro, carboxyl, hydroxyl, hydroxyalkyl, alkoxy, or other water soluble sidechain, and Y is a sidechain comprising hydrogen, alkyl, hydroxyalkyl, carboxyl, aryl, alkenyl, cycloalkanes, cycloalkenes, water soluble sidechains, amino acids, peptide, and any of the foregoing attached to the terminal carbon by an ether, ester, carbonyl, or glycosidic linkage, and a pharmaceutically acceptable carrier therefor. As will be appreciated by those skilled in the art, the particular pharmaceutical carrier can be saline solution incorporating suitable stabilants, buffers, antimicrobial agents, antifungal agents, or other such additions as required for storage and delivery. In addition, the present invention contemplates lyophilized storage, with activation upon mixing, or any other storage technique known and utilized by those skilled in the pharmaceutical arts.

Still another aspect of the present invention is the use of the foregoing described synthetically derived quassinoids, or previously known, purified and isolated quassinoids, for treatment in conjunction with suitable pharmaceutical carriers of viral infections. Viral infections may include rhinoviruses, pseudorabies, or retroviral infections such as human immunodeficiency virus (HIV). Advantageously, certain compounds according to the present invention are believed to preferentially target virally infected cells, instead of acting against isolated viral particles.

As will be appreciated by those skilled in the art, the particular pharmaceutical carrier for use in conjunction with the antiviral compounds of the present invention can be saline solution incorporating suitable stabilants, buffers, antimicrobial agents, antifungal agents, or other such additions as required for storage and delivery. In addition, the present invention contemplates lyophilized storage, with activation upon mixing, or any other storage technique known and utilized by those skilled in the pharmaceutical arts.

Another aspect of the present invention is the preparation of an impermeant quassinoid conjugate that is active against a cancer-specific isoform of a plasma membrane NADH oxidase (tNOX) with characteristics of pancancer anticancer agents. Its use or use of conjugates of other members of the quassinoid series as broad-spectrum anticancer drugs is indicated.

The opportunities for conjugation are broad. The principal requirements are that the conjugating materials render the quassinoid impermeant and do not interfere with its ability to inhibit growth through the cell surface site. Additionally, the materials having therapeutic utility would be expected to benefit from being non-toxic and non-immunogenic and should result in conjugates that are water soluble and/or easy to administer. Active species in high yield and efficacy at low cost would constitute additional desirable properties.

Examples of suitable conjugating materials include polyethyleneglycol, dextran, dextrins, carboxymethylcellulose, polyoxyethylene/polyoxypropylene (polyoxamine) blockpolymers, polyglutamine and other polyamines, N-(2-hydroxypropyl) methacrylamide copolymers, and other polymers properly functionalized to allow facile and functional conjugate formation. The degree of polymerization of the polymer in the polymeric-drug conjugate may vary from N=1 to N=1000 or more as long as the final conjugate is impermeant, effective and is able to reach the target site to deliver therapeutic levels of drug. The linkage may be non-hydrolyzable or hydrolyzable and may contain one or more space atoms optimized to enhance efficacy.

To aid in effective delivery of an anticancer or antiviral agent of the present invention to a desired body site, targeting agents such as monoclonal antibodies, chemical compounds differentially uptaken by cancerous or virally infected cells, or agents known to target cancerous or virally infected tissue (eg. hepatic tissue targeted by acetaminophen derivatives or glycosaccharides) can be conjugated to the compounds of the present invention. As those skilled in the art will appreciate, intravenous delivery is preferred, although topical, oral, or subcutaneous delivery may also be appropriate in specific situations.

In order to prepare conjugates that impact specificity of targeting, quassinoids can be combined variously with, for example, proteins, antibodies, nucleic acids, or even lipids or derivatized polymeric substances and various naturally occurring macromolecules such as immunoglobulins, growth hormones, insulin, interferons, plasma albumin, fibrinogen, plasminogen activator, heparin, chondroitin sulfate, soybean trypsin inhibitor, L-asparaginase, ribonuclease, etc. that would function as homing receptors or targets to a specific cell type (e.g., cancer cells) or location (e.g., bone marrow).

One more aspect of the present invention is the use of the foregoing described synthetically derived quassinoids, or previously known, purified and isolated quassinoids, for use as an NADH oxidase inhibitor. This use is believed to account for differential cytotoxicity of compounds according to the present invention, as well as for herbistatic activity of the compounds.

Additional objects, features, and advantages of the present invention will be apparent upon consideration of the following detailed description and accompanying drawings.

DETAILED DESCRIPTION OF THE INVENTION

Isolation, purification, synthesis, and utility of quassinoids is described in the following examples. As those skilled in the art will appreciate, isolation of novel quassinoids subject to the present invention is possible not only from the roots of *Castela peninsularis*, but from other Castela species, subspecies, or varieties, and from related members of the family Simaroubaceae. Purification and separation of novel quassinoids may proceed from the use of solvent extracts such as methanol, ethanol, aromatic solvents, or other suitable extracting agents;

Synthesis embraces everything from minor sidechain additions or subtractions from the picrasane carbon skeleton, to complete synthesis as disclosed in Grieco et al., "Synthetic Studies on Quassinoids: Total Synthesis of (−)-Chaparrinone, (−)-Glaucarubolone, and (+)Glaucarubinone", Jour.Am.Chem.Soc. 1993, 115, pp.6078–6093, the disclosure of which is herein incorporated by reference. As will be apparent from this disclosure, numerous compounds within the scope of the present invention and having sidechain modifications at the C-15 site have been naturally isolated or synthesized.

Therapeutic utility of compounds of the present invention primarily rests on evidence derived from cell culture studies and live animal experiments. Activity against solid tumor cancers, virally infected cells, differential cytotoxic activity based on NADH oxidase inhibition, and herbicidal and herbistatic activity is detailed in the following examples.

However, as those skilled in the art will appreciate, a wider scope of therapeutic activity for certain compounds may also exist.

EXAMPLE 1

Isolation and Identification of Peninsularinone and Glaucarubolone

Figure 1:
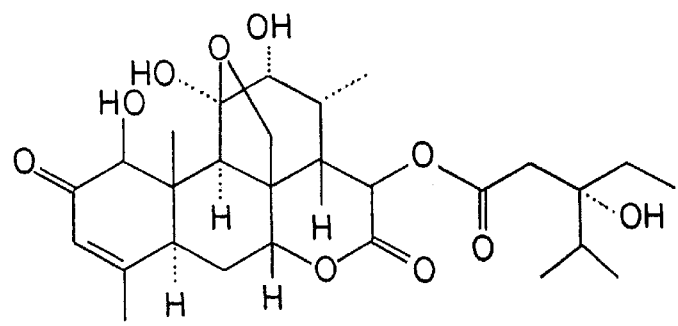
FIG. 1 illustrates the chemical structure of peninsularinone.
Figure 2:
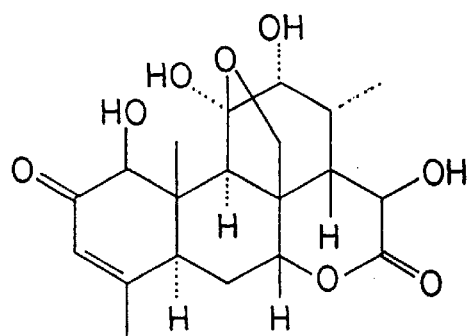
FIG. 2 illustrates the chemical structure of glaucarubolone, purified and isolated from natural sources.
Figure 3:
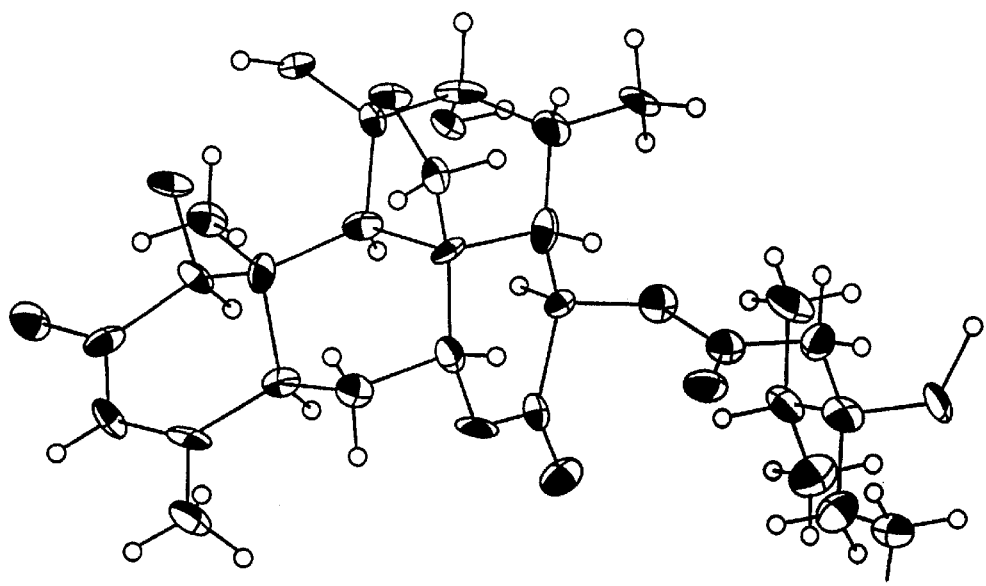
FIG. 3 illustrates the ORTEP derived physical structure of peninsularinone as seen in FIG. 1.
Figure 4:
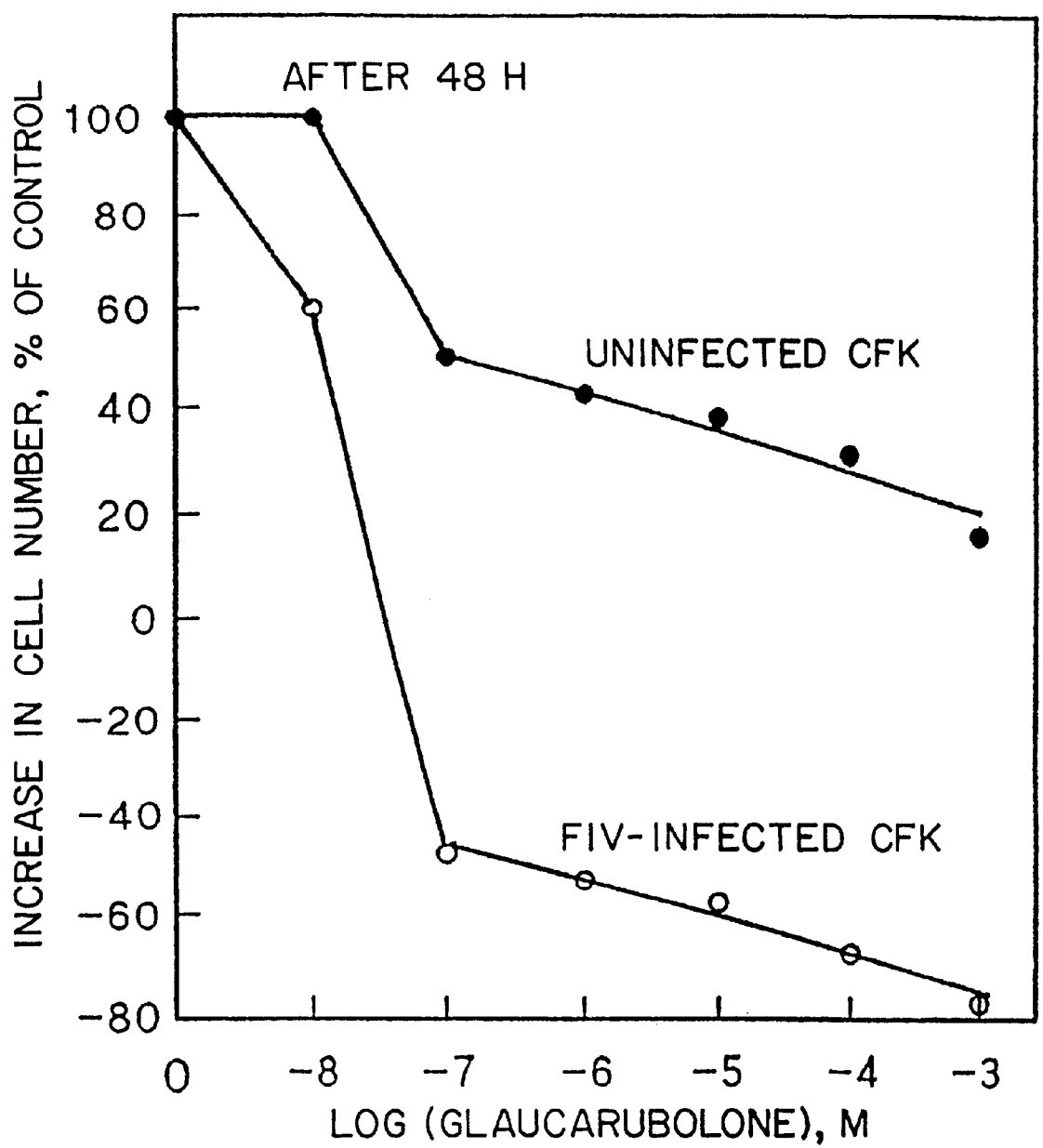
FIG. 4 is a graph comparing log concentration of glaucarubolone to the increase in cell number of feline immunodeficiency virus (FIV) infected cells and uninfected control cells after 48 hours.
Figure 5:
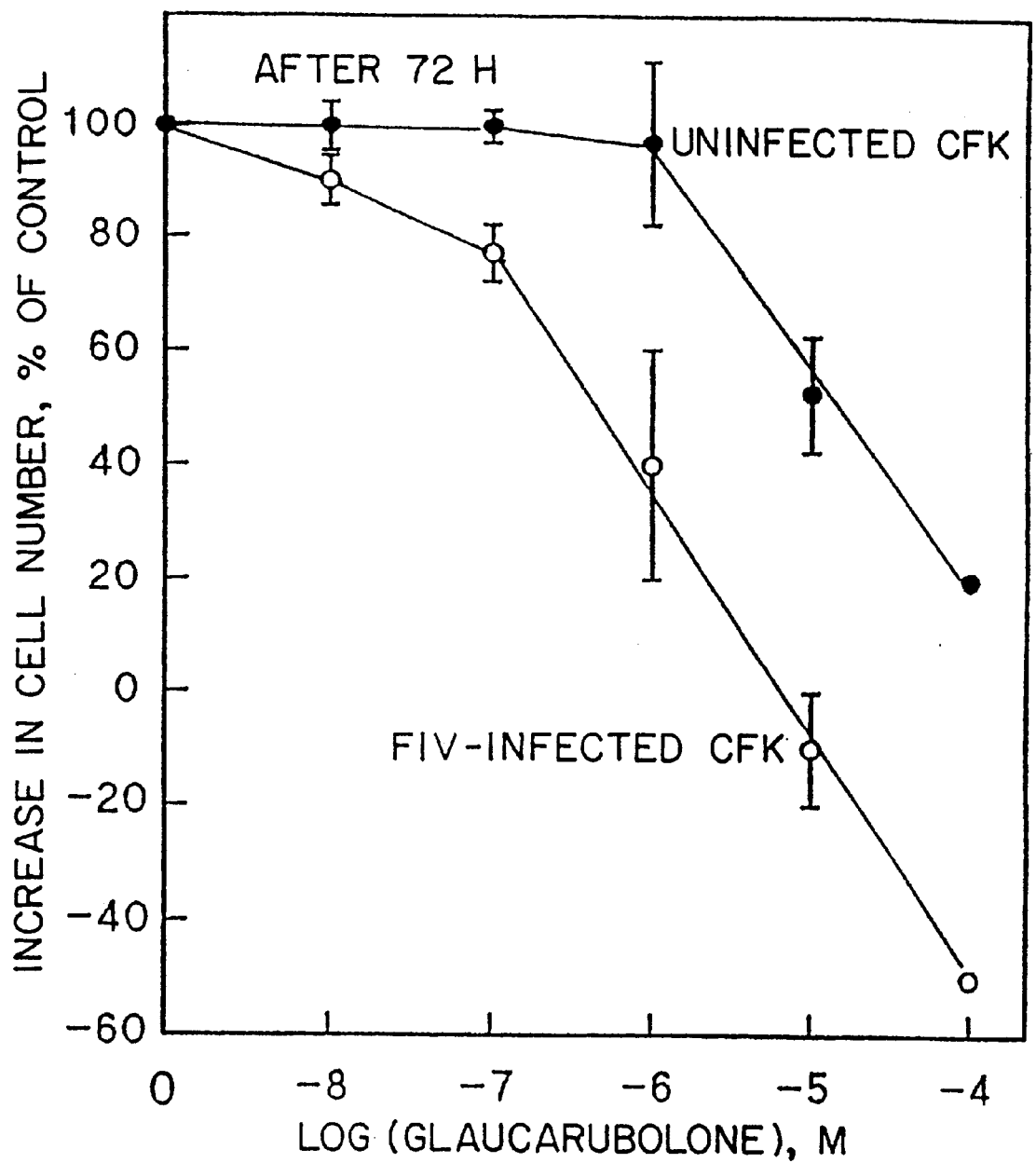
FIG. 5 is a graph comparing log concentration of glaucarubolone to the increase in cell number of feline immunodeficiency virus (FIV) infected cells and uninfected control cells after 72 hours.

Isolation and characterization of a new quassinoid (−)-peninsularinone (See FIG. 1) along with a previously identified quassinoid, glaucarubolone (See FIG. 2) was accomplished by use of methanol extracts of the roots of *Castela peninsularis*. The structure of glaucarubolone was identified by comparison of the $^1H$ and $^{13}C$ NMR spectra of naturally isolated and purified glaucarubolone with those obtained from synthetic glaucarubolone.

The structure of peninsularinone was determined by a combination of $^1H$ and $^{13}C$ NMR spectroscopy, mass spectrometry, and x-ray crystallography. The mass spectrum of peninsularinone indicated a molecular formula of $C_{28}H_{40}O_{10}$. In addition, the mass spectrum exhibited a major peak at $M-C_8H_{15}O_3$. A comparison of the $^1H$ and $^{13}C$ NMR spectra of the peninsularinone with those of glaucarubolone revealed that the spectra were very similar and suggested that the C(15) hydroxyl of glaucarubolone was acylated. In keeping with the mass spectral data, the $^{13}C$ NMR spectrum clearly revealed eight additional carbon atoms: one carbonyl (168.4 ppm), a quaternary carbon bearing an oxygen (75.4 ppm), two methylenes (40.8 and 29.6 ppm), three methyl groups (17.2, 17.4, and 8.3 ppm), and one methine carbon (34.7 ppm). The $^1$H NMR spectrum exhibited an AB quartet centered at δ 2.88 (J=15 Hz) which together with the $^{13}$C data suggested the presence of a methylene adjacent to carbonyl and a quaternary carbon possessing an oxygen atom: C(q)CH$_2$C=O. Also readily apparent from the proton spectrum was the presence of an isopropyl group and an ethyl group, both presumably attached to the same quaternary carbon bearing a hydroxy group. The absolute configuration of the picrasane carbocyclic framework of the quassinoids follows from biosynthetic considerations, x-ray crystallographic data, and total synthesis. Determination of the absolute configuration of the quaternary carbon in the C-15 sidechain was realized via single crystal x-ray analysis of peninsularinone. Analysis of the x-ray crystallographic data of peninsularinone indicated an orthorhombic crystal (C2, Z=8) with the following dimensions: a=28.538(25)Å, b=6.866(5)Å, c=30.300(26)Å35 and β=116.57(2)°. The volume of the crystal was 5310.13 Å$^3$ with a density of 1.342g cm$^3$.

Proton ($^1$H) and carbon ($^{13}$C) nuclear magnetic resonance spectra were recorded on either a Varian VXR-400 MHz (100 MHz) spectrometer or a Bruker AM-500 MHz (125 MHz) spectrometer as indicated.

Chemical shifts are reported in parts per million (δ) relative to tetramethylsilane (δ0.0). Infrared (IR) spectra were recorded on a Mattson Galaxy 4020 series FTIR spectrometer. Absorption intensities are indicated as strong (s), medium (m), or weak (w). High resolution mass spectra were obtained on a Kratos MS 80/RFAQ spectrometer.

Elemental analyses were performed by Galbraith Laboratories, Inc., Knoxville, Tenn. Melting points were obtained on a Fisher-Johns hot-stage apparatus and are uncorrected. Optical rotations were obtained on a Perkin-Elmer Model 241 Polarimeter. Thin layer chromatography (TLC) was performed using E. Merck precoated silica gel 60 F-254 (0.25 mm thickness) plates. The plates were visualized by immersion in a p-1 anisaldehyde solution and warming on a hot plate. E. Merck silica gel 60 (230–400 mesh) was used for flash silica gel chromatography. All chromatography solvents are reagent grade unless otherwise stated. Fraction collecting commenced after the elution of one solvent front from the column.

Plant material. The roots of *Castela peninsularis* Rose were procured from Baja California on Apr. 18, 1993 by World Botanical Associates.

Extraction and isolation. Dried, ground roots (962 g) were soaked in 2800 ml of methanol. After 3 days the plant material was drained and rinsed with methanol (1×2800 ml). The process was repeated on the same 962 9 of plant material a total of 9 times. The combined methanol extracts and washings were concentrated in vacuo to a brown sludge (ca. 120 g) which was diluted with 20% methanol/chloroform (1000 ml), stirred for 24 h, and filtered through a pad of flash silica gel, washing well with 20% methanol/chloroform). The filtrate and washings were concentrated in vacuo to a brown oil (ca. 32 g). The brown oil was chromatographed on 690 g of flash silica gel (packed in 10% methanol/chloroform). The column was successively eluted, collecting 150 ml fractions: fractions 3–16 (portion 1) were combined and concentrated in vacuo providing 19 g of a brown sludge; fractions 17–28 (portion 11) were combined and concentrated in vacuo leaving 2.0 g of a yellow foam.

Portion I (19 g) was chromatographed on 400 g of flash silica gel (packed in 3:1/ethyl acetate-hexanes). The column was successively eluted, collecting 75 ml fractions: fractions 48–66 (IA) (3:1/ethyl acetate:hexanes) were combined and fraction 67–98 (IB) (5:1/ethyl acetate:hexanes) were combined. Fractions 48–66 (IA) were concentrated in vacuo to a faint yellow solid (684 mg) which crystallized from ethyl acetate providing 161 mg of 2 as long needles. The mother liquor was chromatographed on 130 g of flash silica gel (packed in 2% methanol/chloroform). The column was successively eluted, collecting 40 ml fractions: fractions 43–49 (5% methanol/chloroform) were collected and combined to provide another 216 mg of 2 as a white solid. Portion IB was concentrated in vacuo to a yellow foam (864 mg) that was chromatographed on 125 g of flash silica gel (packed in 5% methanol/chloroform). The column was successively eluted, collecting 12 ml fractions: fractions 43–55 were combined and concentrated in vacuo leaving an off-white solid (371 mg) which crystallized from ethyl acetate providing 148 mg of 1 as small white needles. Purification of the mother liquor by preparative thin layer chromatography (11 plates, 0.5 mm thickness, 5% methanol/chloroform, double elution) afforded another 94 mg of 1 as a white solid.

Portion 11 (2.0 g) was chromatographed on 200 g of flash silica gel (packed in ethyl acetate). The column was successively eluted, collecting 40 ml fractions: fractions 17–41 were combined and concentrated in vacuo providing 681 mg of crystalline glaucarubolone which was identified by comparison of its spectroscopic data (IR, MS, $^1$H NMR, $^{13}$C NMR) with those reported previously in the literature.

(–)-Peninsularinone 1: Rf 0.14 (ethyl acetate:hexanes, 2:1), 0.20 (5% methanol/chloroform); FTIR (KBr) 3520 (s), 2969 (m), 2884 (m), 1728 (s), 1680 (s), 1460 (w), 1385 (w), 1254 (m), 1229 (m), 1192 (m), 1115 (m), 988 (w), 961 (w), 916 (w) cm$^{-1}$; 400 MHz $^1$H NMR (C$_5$D$_5$N)δ9.78 (br s, 1H), 9.43 (br s, 1H), 7.46 (d, 1H, J=3.6 Hz), 6.42 (d, 1H, J=11.2 Hz), 6.09 (s, 1H), 4.79 (s, 1H), 4.23 (s, 1H), 4.14 (d, 1H, J=8.6 Hz), 4.03 (br s, 1H), 3.83 (d, 1H, J=8.6 Hz), 3.39 (s, 1H), 3.09 (br d,1H, J=12.4 Hz), 2.95 and 2.81 (AB quartet, 2H, J=15 Hz), 2.66–2.54 (m, 2H), 2.25–2.10 (m, 2H), 2.08–1.85 (m, 3H), 1.71 (s, 3H), 1.55 (s, 3H), 1.39 (d, 3H, J=Hz), 1.12–1.01 (m, 9H); 100 MHz $^{13}$C NMR (C$_5$D$_5$N) δ 197.38, 172.02, 168.36, 162.29, 126.16, 110.73, 84.34, 79.97, 78.56, 75.41, 71.30, 70.78, 48,09, 45.99, 45.58, 45.44, 42.19, 40.85, 34.69, 32.74, 29.59, 25.90, 22.34, 17.45, 17.23, 15.52, 10.74, 8.30. High-resolution MS (Cl) calcd. for C$_{28}$H$_{41}$O$_{10}$ (M+1) m/e 537.2700, found 537.2686; C$_{20}$H$_{25}$O$_7$(M-C$_8$H$_{41}$O$_3$) m/e 377.1601, found 377.1594. An analytical sample was prepared by recrystallization from ethyl acetate: mp 221–223° C.; $[\alpha]^{25}_D$ –22.6° (c 0.19, pyridine). Anal. calcd. for C$_{28}$H$_{4010}$: C, 62.67; H,7.51. Found: C,62.34; H,7.62.

X-ray data for peninsularinone: Monoclinic crystals with a=28.538(25), b=6.866(5), c=30.300(26)Å, β=116.57(2)° and V=5310.1(9)Å$^3$ at –172° C. Space group was C2, with Z=8 and D$_{calc}$=1.342 g cm$^{-3}$, F(000)=2304. Reflections were measured on a locally modified Picker goniostat, λ(MoKα)=0.71069 Å. Intensities were measured using a continuous scan mode with fixed backgrounds for 3818 unique reflections of which 2512 were observed (F>2.33σ (F)]. Structure was solved by direct methods (SHELXS-86) and refined by full matrix least squares. Final discrepancy index was R=0.072.

EXAMPLE 2

Quassinoid Analogs

In addition to purified, isolated natural products, the present invention includes sidechain modified analogs to naturally occurring quassinoids. Most importantly, this includes modification to the C-15 side chain, although certain ring structure modifications or varying substituents at the C-4 position are contemplated as within the scope of the present invention.

For example, as seen in the following schematic synthesis scheme (Formulas VII through XIII, hereinafter) starting with glaucarubolone (Formula VIII), it is possible by appropriate chemical modification to produce 15-oxy-(hydroxypivaloyl) glaucarubolone (Formula XI) or 15-oxy-(N,N-dimethylglycine) glaucarubolone (Formula XIII):

MS 80/RFAQ spectrometer. Elemental analyses were performed by Galbraith Laboratories, Inc., Knoxville, Tenn., or by Robertson Microlit Laboratories, Inc., Madison, N.J. Melting points were obtained on a Fisher-Johns hot-stage and are uncorrected. Optical rotations were obtained on a Perkin-Elmer Model 241 polarimeter. Reactions were monitored by thin layer chromatography (TLC) using E. Merck precoated silica gel 60 F-254 (0.25 mm thickness) plates. The plates were visualized by immersion in a p-anisaldehyde solution and warming on a hot plate. E. Merck silica gel 60 (230–400 mesh) was used for flash silica gel chromatography.

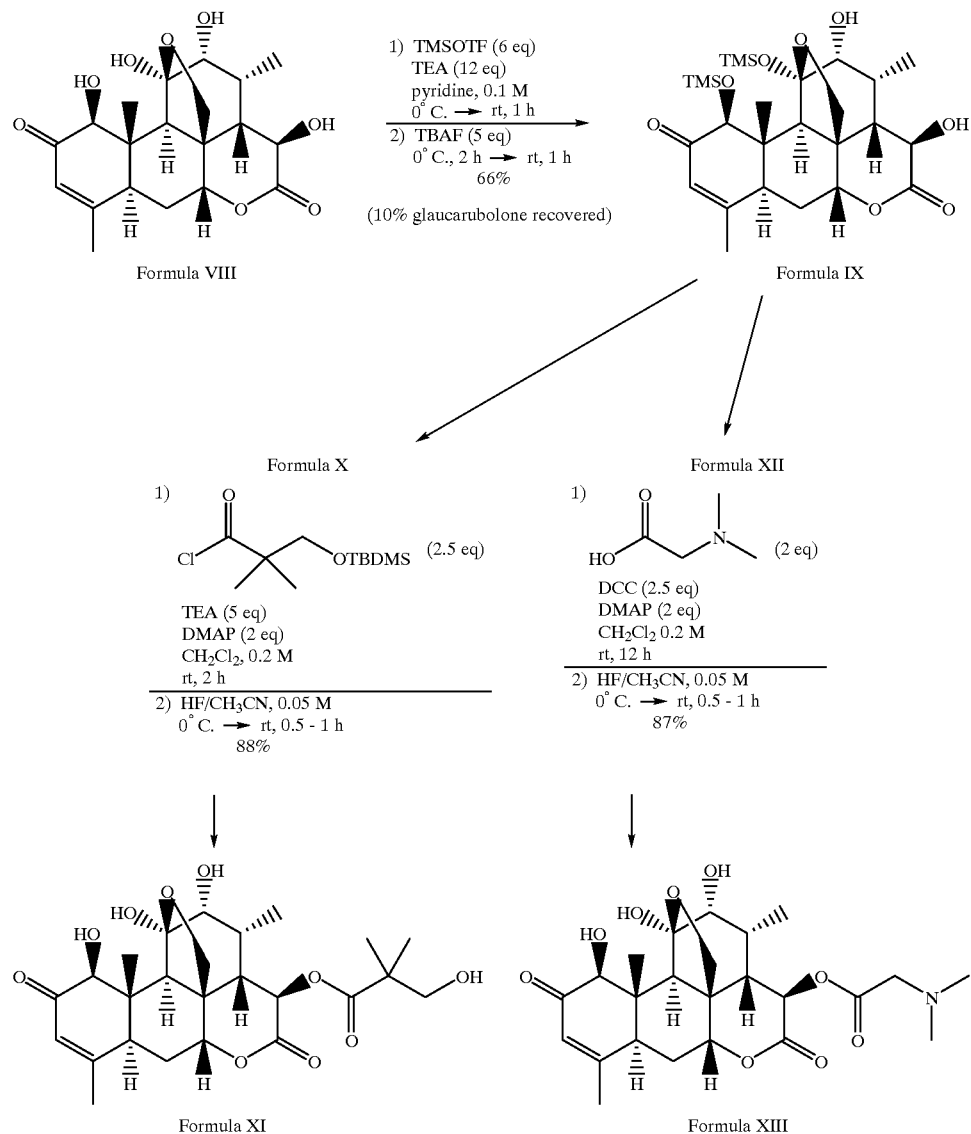

Synthesis and characterization of the above compounds involved proton ($^1$H) and carbon ($^{13}$C) nuclear magnetic resonance spectra recorded on Varian VXR-400 MHz (100 MHz) or a Bruker AM 500 MHz (125 MHz) spectrometers. Chemical shifts are reported in parts per million (δ) relative to tetramethylsilane (δ 0.0). Infrared (1R) spectra were taken on a Perkin-Elmer Model 298 spectrophotometer or on a Mattson Galaxy 4020 series FTIR spectrometer. Absorption intensities are indicated as strong (s), medium (m), or weak (w). High resolution mass spectra were obtained on a Kratos All reactions were conducted in oven dried (110° C.) glassware under an argon atmosphere utilizing anhydrous solvents. All solvents are reagent grade unless otherwise stated. Dichloromethane, triethylamine, 2,6-lutidine, pyridine, chlorotrimethylsilane, and trimethylsilyl trifluoromethanesulfonate were distilled from calcium hydride. Tetrahydrofuran was freshly distilled from sodium benzophenone ketyl.

1,11-Bis(trimethylsilyloxy)glaucarubolone (Formula IX). A solution of 300 mg (0.761 mmol) of glaucarubolone (Formula VIII) in 8.5 ml of pyridine containing 1.3 ml (9.13 mmol) of triethylamine at 0° C. was treated with 898 µl (4.56 mmol) of trimethylsilyl trifluoromethanesulfonate. After warming to room temperature and stirring for 1 h the reaction was recooled to 0° C. and treated with 761 µl (0.761 mmol) of a 1.0 M solution of tetrabutylammonium fluoride in tetrahydrofuran every 30 min until a total of 5 equivalents (3.81 mmol) of the tetrabutylammonium fluoride solution were added. After stirring at 0° C. for an additional 30 min and at room temperature for 30 min the reaction mixture was poured onto 17 ml of a saturated aqueous solution of sodium bicarbonate and diluted with 20 ml of ethyl acetate. The layers were separated and the organic layer was washed with brine (1×17 ml). The combined aqueous layers were washed with ethyl acetate (1×10 ml), dried ($Na_2SO_4$), filtered, and concentrated in vacuo to a brown oil. The oil was chromatographed on 80 g of flash silica gel eluting with ethyl acetate-hexanes (4:1) to afford 270 mg (66%) of 1,11-bis(trimethylsilyloxy)glaucarubolone (Formula IX) as a white solid: Rf 0.72 (ethyl acetate-hexanes, 4:1); IR (Kbr) 3595 (m), 3545 (w), 2970 (m), 2895 (w), 1720 (s), 1690 (s), 1327 (m), 1250 (s), 1190 (s), 1152 (m), 1057 (s), 922 (s), 840 (s), 758 (m), cm$^{-1}$; 400 MHz $^1$H NMR ($C_5D_5N$) δ 7.93 (d, 1H, J=5.2 Hz), 6.04 (br s, 1 H), 5.88 (d, 1H, J=4.8 Hz), 5.32 (dd, 1H, J=11.2, 5.2 Hz), 4.57 (brs, 1H), 4.23 (s, 1H), 4.00 (d, 1H, J=8.2 Hz), 3.88 (t, 1H, J=4.8 Hz), 3.73 (d, 1H, J=8.2 Hz), 3.11–3.02 (m, 1H), 3.06 (s, 1H), 2.54 (m, 1H), 2.26 (dd, 1H, J=11.2, 6.4 Hz), 2.06 (dt, 1H, J=14.2, 2.8 Hz), 1.88 (t, 1H, J=14.2 Hz), 1.71 (s, 3H), 1.66 (d, 3H, J=7.2 Hz), 1.32 (s, 3H), 0.36 (s, 9H), 0.32 (s, 9H); 100 MHz $^{13}$C NMR ($C_5D_5N$) δ 198.49, 174.06, 160.92, 127.08, 113.61, 88.04, 81.02, 77.96, 71.71, 68.58, 49.83, 47.26, 46,04, 44.28, 44.09, 33.55, 25.85, 22.36, 16.25, 10.65, 3.01, 1.55; high-resolution MS (El calcd for $C_{26}H_{42}O_8Si_2$ (M) m/e 538.2419, found 538.2393. An analytical sample was prepared by recrystallization from ethyl acetate: mp 228–230° C. (dec); $[\alpha]_D^{25}$-12.0 (c 0.55, pyridine). Anal. Calcd for $C_{26}H_{42}O_8Si_2$; C, 57.96; H, 7.86. Found C, 57.85; H, 8.09.

15-oxy-(hydroxypivaloyl)glaucarubolone (Formula XI). A solution of 69 mg (0.13 mmol) of 1,11-Bis(trimethylsilyloxy)glaucarubolone (Formula IX) and 31 mg (0.26 mmol) of 4-dimethylaminopyridine in 0.64 ml of dichloromethane was cooled to 0° C. and treated with 89 µl (0.64 mmol) of triethylamine followed by 80 mg (0.32 mmol) of the acid chloride derived from the tert-butyldimethylsilylether of hydroxypivalic acid (Formula X). After warming to room temperature and stirring for 2 h the heterogeneous mixture was diluted with hexanes (1 ml) and filtered through a small plug of silica gel with ethyl acetate (10×1 ml). The filtrate was concentrated in vacuo and the crude residue chromatographed on 20 g of flash silica gel eluting with hexanes-ethyl acetate (5:1) which provided 96 mg (100%) of the desired adduct.

The purified material (96 mg) was dissolved in 2.5 ml of acetonitrile and cooled to 0° C. With stirring, 635 µl of a 1 M solution of hydrofluoric acid in acetonitrile was added and the resulting solution allowed to warm to room temperature and stir for 0.5 h. The reaction was diluted with ethyl acetate-methanol (1:1, 2 ml) and treated with 200 µl of saturated sodium hydrogen carbonate then filtered through a small plug of silica gel with ethyl acetate-methanol (20:1, –10×1 ml). The filtrate was concentrated in vacuo and chromatographed on 20 g of flash silica gel eluting with chloroform-methanol (10:1) which provided 55.8 mg (88%) of (Formula XI) as a white solid: Rf 0.19 (chloroform-methanol, 10:1); IR (Kbr) 3517 (s), 3468 (s), 2974 (m), 2928 (m), 1746 (s), 1715 (s), 1682 (s), 1383 (m), 1248 (m), 1121 (s), 1053 (s) cm$^{-1}$; 500 MHz $^1$H NMR ($C_5D_5N$) δ 9.74 (br s, 1H), 9.41 (br s, 1H), 7.44 (d, 1H, J=4.7 Hz), 6.40 (br d, 1H, J=11.7 Hz), 6.27 (br t, 1H, J=6.0 Hz), 6.09 (br s, 1H), 4.81 (br s, 1H), 4.19 (br s, 1H), 4.13 (d, 1H, J=8.8 Hz), 4.05–3.98 (m, 3H), 3.79 (d, 1H, J=8.8. Hz), 3.37 (s, 1H), 3.10 (br d, 1H, J=13.3 Hz), 2.67 (dd, 1H, J=11.7, 6.3 Hz), 2.59 (m, 1H), 2.14 (dt, 1H, J=14.5, 3.2 Hz), 2.00 (br t, 1H, J=14.5 Hz), 1.70 (s, 3H), 1.55 (s, 3H), 1.48 (s, 6H), 1.46 (d, 3H, J=7.4 hz); 125 MHz $^{13}$C NMR ($C_5D_5N$) δ 197.26, 176.38, 168.54, 162.41, 126.13, 110.67, 84.40, 80.09, 78.46, 71.33, 71.21, 69.43, 48.19, 46.23, 45.59, 45.45, 42.23, 32.81, 25.93, 22.25, 22.23, 22.17, 15.71, 10.70. An analytical sample was prepared by recrystallization form ethyl acetate-methanol. mp 259–261° C.; $[\alpha]_D^{25}$-17.1 (c 0.59, pyridine). Anal. calcd. for $C_{25}H_{34}O_{10}$: C, 60.72; H, 6.93. Found: C, 60.63; H, 6.92.

15 oxy-(N,N-dimethylglycine)glaucarubolone(Formula XIII). 10 mg (0.02 mmol) of 1,11-bis(trimethylsilyloxy) glaucarubolone (Formula IX), 4 mg (0.04 mmol) of N,N-dimethylglycine (Formula XII), 5 mg (0.04 mmol) of 4-dimethylaminopyridine and 10 mg (0.04 mmol) of 1,3dicyclohexylcarbodiimide were combined in a small vial. Dichloromethane (93 µl) was added and the resulting solution allowed to stir at room temperature for 12 h. The heterogeneous mixture was filtered through a small plug of silica gel with ethyl acetate (10×1 ml) and the filtrate concentrated in vacuo. Chromatography on 10 g of flash silica gel eluting with chloroform-methanol (20:1) provided the crude product, still heavily contaminated with dicyclohexyl urea.

The crude product (20.3 mg) was dissolved in 370 µl of acetonitrile and cooled to 0° C. With stirring, 185 µl of a 1 M solution of hydrofluoric acid in acetonitrile was added and the resulting solution was stirred at 0° C. for 0.5 h. An additional 185 µl of a 1 M solution of hydrofluoric acid in acetonitrile was added and the solution allowed to warm to room temperature and stir for 0.5 h. The reaction was diluted with 200 µl of water, then sodium hydrogen carbonate 50 mg (0.60 mmol) was added and the mixture stirred at room temperature until no more effervescence was noted. The mixture was filtered through a small plug of silica gel with ethyl acetate-methanol (20:1, 10×1 ml). The filtrate was concentrated in vacuo and chromatographed on 10 g of flash silica gel eluting with chloroform-methanol (20:1→5:1) which provided 7.7 mg (87%) of (4) as a white solid: Rf 0.30 (chloroform-methanol, 5:1); IR (Kbr) 3520 (m), 3395 (m), 2944 (m), 2890 (m), 1740 (s), 1674 (s),1458 (w), 1385 (w), 1229 (m), 1192 (m), 1049 (m) cm$^{-1}$; 500 MHz $^1$H NMR ($C_5D_5N$ δ 9.78 (br s, 1H), 9.45 (br s, 1H), 7.46 (d, 1H, J=4.7 Hz), 6.51 (br d, 1H, J=11.3 Hz), 6.10 (br s, 1H), 4.78 (br s, 1H), 4.24 (br s, 1H), 4.15 (d, 1H, J=8.8 Hz), 4.03 (brt, 1H, J=4.7 Hz), 3.85 (d, 1H, J=8.8 Hz), 3.43 (apparent q, 2H, J=16.6 Hz), 3.40 (s, 1H), 3.08 (br d, 1H, J=12.4 Hz), 2.58 (m, 2H), 2.38 (s, 6H), 2.16 (dt, 1H, J=14.7, 2.8 Hz), 2.03 (br t, 1H, J=14.7 Hz), 1.73(s, 3H), 1.56 (s, 3H), 1.32 (d, 3H, J=6.7 Hz); 125 MHz $^{13}$C NMR ($C_5D_5N$ 6197.36, 170.15, 168.12, 162.22, 126.16, 110.73, 84.29, 79.90, 78.55, 71.27, 70.43, 60.64, 48.00, 46.06, 45.51, 45.45, 45.04, 42.16, 32.69, 25.88, 22.28, 15.32, 10.65.

Of course, additional sidechain modifications, such as additions at the hydroxyl of Formula XI or the amine of Formula XIII are within the scope of the present invention. As those skilled in the art will appreciate, synthetic methods employed for the foregoing novel compounds can be extended to encompass alternative C-15 sidechains with differing selectivity, toxicity, potency, solubility, and therapeutic effectiveness.

EXAMPLE 3

Anticancer Activity of Peninsularinone, Glaucarubinone, and Related Analogs

When Glaucarubinone (FIG. 1) was examined in vitro, it was found to be solid tumor selective (Table 1, hereinafter) demonstrating a zone differential of 400 units between C38 and L1210 (at 1 ug/disk). A similar, or greater differential was noted for PO3 while no differential was found for M17/Adr, indicating a likely cross-resistance with other natural products such as Adriamycin. Furthermore, depending upon the human cell line used in the assay, differential cytotoxicity was (H125, MX-1) or was not (CX-1, H-8) demonstrable.

Subsequent in vivo testing (Table 2, hereinafter), demonstrated curative activity against both C38 and PO3. Antitumor activity was also noted against the two other tumor models studied, Col26 and Mam 16/C. One of the most intriguing findings with this compound was that the dose could be escalated during the treatment to over an order of magnitude difference from the start of therapy; that is, supralethal doses of glaucarubinone could be administered if the animals had been pretreated for a few days with lower, non-toxic doses of the compound.

Quassinoid analogs having different substituents at the C-15 position were also examined for anticancer activity. The results of five such compounds are presented in Table 1.

Surprisingly, while Ailanthinone, which lacks a hydroxyl group in the C15 chain, had a similar potency to Glaucarubinone, it demonstrated no solid tumor selectivity. Because of this, it was not tested in vivo. However, as the side chain diminished in length, the remaining 3 compounds, Holacanthone (the acetate ester), Glaucarubolone (the hydroxy analog), and chapparinone (in which the C-15 side chain is missing), not only demonstrated solid tumor selectivity to both murine and human cells but also demonstrated selectivity to a multidrug resistant, p-glycoprotein expressing mammary tumor (Mam 17/Adr). Finally, a recent acquisition, peninsularinone, which has 2 Carbons more than Glaucarubinone, appears similar in potency and spectrum of activity as Glaucarubinone.

Two of these compounds, Glaucarubolone and Chaparrinone were studied in vivo. As shown in Table 2, both had therapeutic activity against C38, with the latter compound having activity also against Mam 16/C and Mam 17/Adr. As observed in the in vitro studies, the potency of both Glaucarubinone and Chaparrinone both were about an order of magnitude less than Glaucarubinone, this is also observed for the in vito studies.

TABLE 1

CHANGES AT THE C-15 POSITION

| | | ZONE UNITS | | | | |
|---|---|---|---|---|---|---|
| COMPOUND | C-15 Sidechain | L1210 | C38 | M17/Adr | CX-1 | H8 |
| GLAUCARBINONE NSC-132791 | $-O-C(=O)-C(CH_3)(OH)-C_2H_5$ | 5:600<br>1:300<br>0.3:160 | 950<br>700<br>450 | —<br>250<br>220 | 400 | 600 (MX-1) |
| AILANTHINONE NSC-238187 | $-O-C(=O)-CH(CH_3)-C_2H_5$ | 2:290 | 340 | — | 300 | — |
| HOLACANTHONE NSC-126765 | $-O-C(=O)-CH_2$ | 12:310 | 950 | — | 900 | — |
| GLAUCARUBOLONE NSC-126764 | —OH | 25:100 | 900 | >950 | 100 | 650 |
| CHAPARRINONE | —H | 5:200 | 920 | 700 | 480 | 270 |
| PENINSULARINONE EDMX-63-II | $-O-C(=O)-CH_2-C(C_2H_5)(OH)-CH_2-CH_2$ | 0.25:310 | 700 (P388) | 420 | — | 510 |

TABLE 2

IN VIVO RESULTS

| Agent | Tumor | IV Schedule* | MTD Total Dose mg/kg | % T/C | Log Cell Kill | Cures |
|---|---|---|---|---|---|---|
| Glaucarubinone | C38 | 3, 5–10 | 9.1 | 12 | — | 1/5 |
| | C16 | 3,5,7,9,11,13 (Twice Daily) | 18 | 42 | — | 0/5 |
| | PO3 | 4–15 | 16 | 15 | 1.5 | 1/6 |
| | PO3 | 4,6,8,10,12,14 (Twice Daily) | 16 | 0 | 3.1 | 0.6 |
| | MAM 16/C | 1–11 | 24 | 10 | 1.5 | 0.5 |
| Holacanthone | C38 | 3–12 | 188 | 11 | 1.4 | 0.5 |
| | MAM 16/C | 1–9 | 80 | 46 | — | 0.5 |
| Glaucarubolone | C38 | 3–6 | 151 | 16 | — | 1/5 |
| Chaparrinone | C38 | 3–9 | 232 | 0 | — | 3/5 |
| | MAM 16/C | 1–6 | 90 | 26 | — | 0/4 |
| | MAM 17/AdR | 1–10 | 260 | 42 | — | 0/5 |
| Peninsularinone | PO3 | 3–13 | 4.3 | 3 | 2.0 | 0/5 |

Mice. Inbreds mice used were C57B1/6, C3H/He, Balb/c, and DBA/2; hybrids were: B6D2F1 (C57B1/6 females× DBA/2 males), and CD2F1 (Balb/c females×DBA/2 males). All mice were obtained from the Frederick Cancer Research Facility, Frederick, Md.

Tumors. The following transplantable solid tumors of mice were used for in vitro and/or in vivo testing; pancreatic ductal adenocarcinoma #02[P02](3), pancreatic ductal adenocarcinoma #03 [P03], colon adenocarcinomas #07/A [C7], #38 [C38] and #51/A [C51], undifferentiated colon carcinoma #26 [C26], mammary adenocarcinoma #16/C [Mamm 16/C], 17/A [Mamm 17] and 17/A/ADR [Mamm 17/Adr]. The leukemias used were the L1210, P388, lymphocytic leukemia, and C1498 myelogenous leukemias. All tumors are in the Developmental Therapeutics Program (DTP) frozen tumor repository, maintained by the Biological Testing Branch, Frederick, Md. Each has a detailed description, code identification number, and list of references at the National Tumor Repository.

Tumors were maintained in the mouse strain of origin and were transplanted into either an appropriate Fl hybrid or the strain of origin for therapy trials. All mice were over 17 g at the start of therapy; the range of individual body weights in each experiment was within 2 g. The mice were supplied food and water ad libitum.

The following human tumors were used: Human adenosquamous lung tumor H-125 (7) and colon tumors H8, HCT-116, and CX-1 were used for in vitro testing only. Each human cell line was maintained in culture until plating was done. HCT-116, H8, and CX-1 were maintained in McCoy's media and heat inactivated fetal bovine serum (11% FBS). It was passaged (1:5 dilution) twice week following enzymatic dissociation using a trypsin/PBS-EDTA mixture. H-125 was maintained in CMRL/Fischer media (1:1) with 11% FBS. It was mechanically dissociated and passaged (3:10 dilution) weekly. For the plating assay, all cells were mechanically dispersed and diluted in the CMRL/Fischer media mixture.

Antitumor Agents. The compound easily dissolved in the diluent which consisted of 3% [V/V (100%-Pure)] Ethanol, 1% (V/V) polyoxyethylanesorbitan monopalmitate (P.O.E.40) and 96% sterile distilled water. The primary route of administration was intravenous (IV).

In Vitro Studies. For this assay, leukemia and solid tumor cells were plated in soft agar. The drug was placed on a filter-paper disk, which was then placed on top of the soft agar containing the tumor cells (9,10). Briefly, a hard bottom layer [containing tryptic soy broth (0.8%), noble-agar (0.8%), the CMRL/Fischers media and horse serum (11%) at 480] was poured into 60 mm plastic dishes (3 ml in each), allowed to solidify and stored at 37° in 5% $CO_2$. Bottom layers were used 4 to 10 days after preparation. A soft agar top layer, containing noble agar (0.44%), the CMRL/Fischers media, horse serum (11%) and titered tumor cells was poured on top and allowed to solidify.

A volume of 50 μl of each drug dilution in ethanol was added to 6.5 mm disks which were allowed to dry and then placed in the tumor cell-containing dish. The plates were incubated for 6 to 10 days and examined on an inverted microscope (40× magnification). Depending upon the innate sensitivity of the cells for the drug (and the concentration of the drug), a zone of inhibition of colony formation occurred. The zone of inhibition (measured from the edge of the disk to the first colonies) was determined in units: 200 units=6.5 mm (the size of the filter paper disk).

Cell Preparation. Both the mouse solid tumors and the leukemia L1210 were passaged SC in the appropriate inbred mice. P388 was maintained in tissue culture passage for the in vitro studies reported.

Cells for the in vitro assay were derived directly from these SC passage tumors as discussed previously. Titers were adjusted to produce about 500 colonies per dish.

In Vivo Chemotherapy. The methods of protocol design, tumor transplantation, drug treatment, endpoint determination, definition of terms, toxicity evaluation, data analysis, quantification of tumor cell kill, and the biologic significance of the drug treatment results with transplantable tumors have been presented. The following is a brief summary of those methods as they apply to the work described.

The animals necessary to begin an experiment were pooled, implanted bilaterally SC on day 0 with 30 to 60 mg tumor fragments using a 12 gauge trocar, and again pooled before randomization to the various treatment and control group. Chemotherapy was either started within 3 days after tumor implantation while the number of cells per mouse was relatively small ($10^7$ to $10^8$ cells), or allowed to grow to palpation (about $3 \times 10^8$ cells) in a more advanced stage trial.

Tumors were measured with a caliper either once or twice weekly (as needed) until either tumors exceeded 1500 mg or cure was assured. Tumor weights were estimated from two-dimensional measurements:

Tumor Weight $(mg) = (a \times b^2)/2$, where a and b are the tumor length and width (mm) respectively.

End Points for Assessing Antitumor Activity. The following quantitative end points were used to assess antitumor activity:

Tumor growth delay. (T-C value), where T is the median time (in days) required for the treatment group tumors to reach a predetermined size, and C is the median time (in days) for the control group tumors to reach the same size. Tumor-free survivors were excluded from these calculations (cures were tabulated separately).

Calculation of tumor cell kill. For SC growing tumors, the $\log_{10}$ cell kill was calculated from the following formula:

$$\text{Log}_{10}\text{kill (total)} = \frac{T - C}{(3.32)(Td)}$$

Where T-C is the tumor growth delay (in days) as described above and Td is the tumor volume doubling time (in days), the latter estimated from the best fit straight line from a log-linear growth plot of the control-group tumors in exponential growth (500 to 1500 mg range). The conversion of the T-C values of $\log_{10}$ cell kill is possible because the Td for tumors regrowing post-treatment approximated the Td values of the tumors in untreated control mice.

Determination of activity by tumor growth inhibition (T/C value). Measurements were carried out simultaneously in both the treatment and control groups. When the control group tumors reached approximately 750–1500 mg in size (median of group), the median tumor weight of each group was determined (including zeros). The T/C value in percent is an indication of antitumor effectiveness. A T/C equal to or less than 42% is considered significant antitumor activity. A T/C value<10% is indicative of a high degree of antitumor activity and is the level used by NCI to justify further development if other requirements are met (termed DN-2 level activity).

A weight loss nadir of 20% per mouse or greater (mean of group) or 20% or more drug-deaths is considered an excessively toxic dosage. Animal body weights included the weights of the tumors.

EXAMPLE 4

Antiviral and NADH Oxidase Inhibition Activity

Purified and isolated glaucarubolone and certain synthetic analogs were also tested for potential antiviral and anti NADH oxidase activity. As indicated in FIGS. 4–7 and Tables 3–5, hereinafter, glaucarubolone and identified analogs in a series of experiments exhibited effective antiviral activity against rhinoviruses, pseudorabies, and retroviruses such as feline immunodeficiency virus (FIV) and human immunodeficiency virus (HIV). NADH oxidase inhibition with glaucarubolone was observed in both animal cell culture and excised tissue segments from plants.

Figure 6:
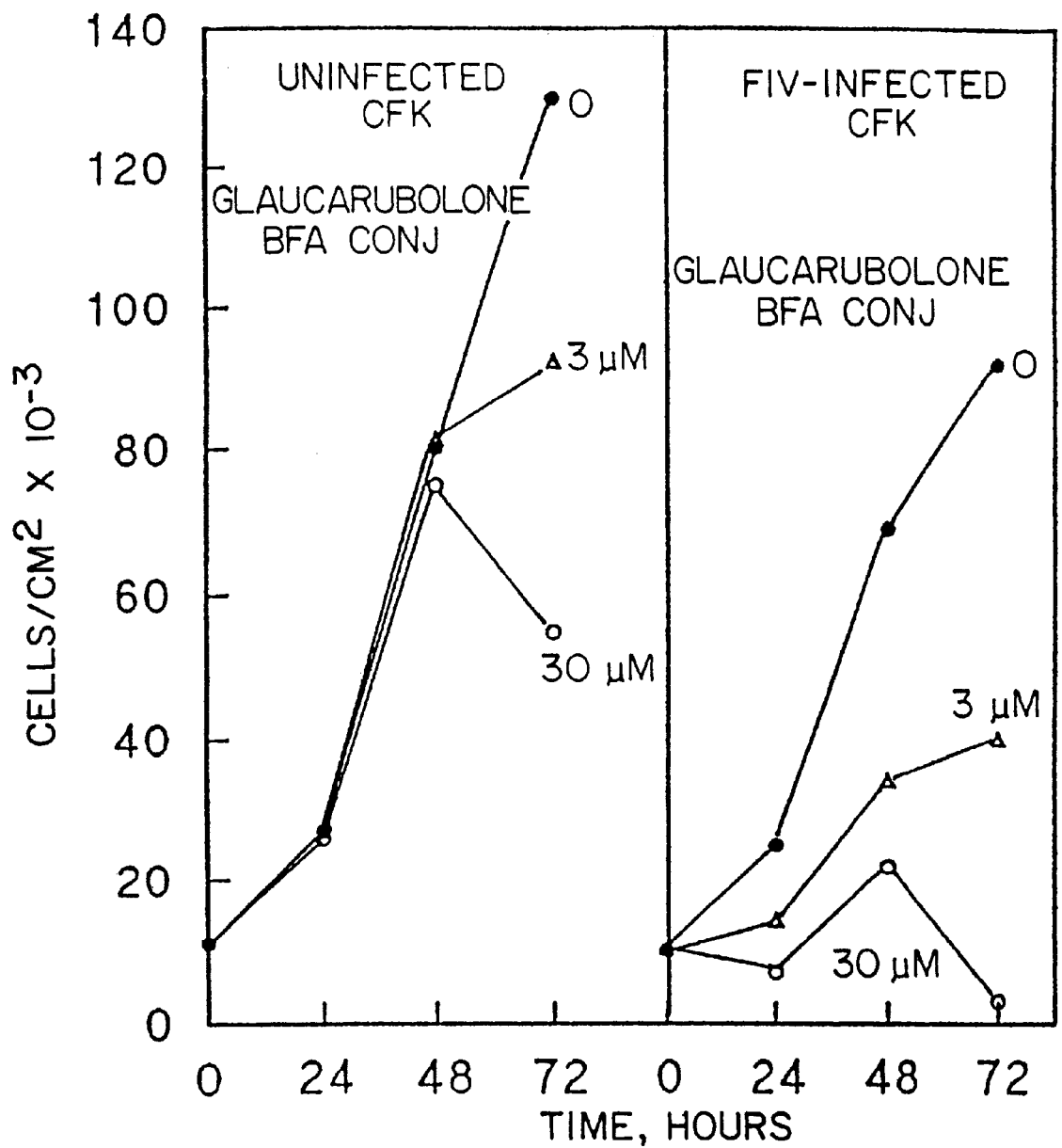
FIG. 6 is a graph comparing cell concentration against time for. feline immunodeficiency virus (FIV) infected and control Crandall Feline Kidney cells contacted with a glaucarubolone-brefeldin A conjugate.
Figure 7:
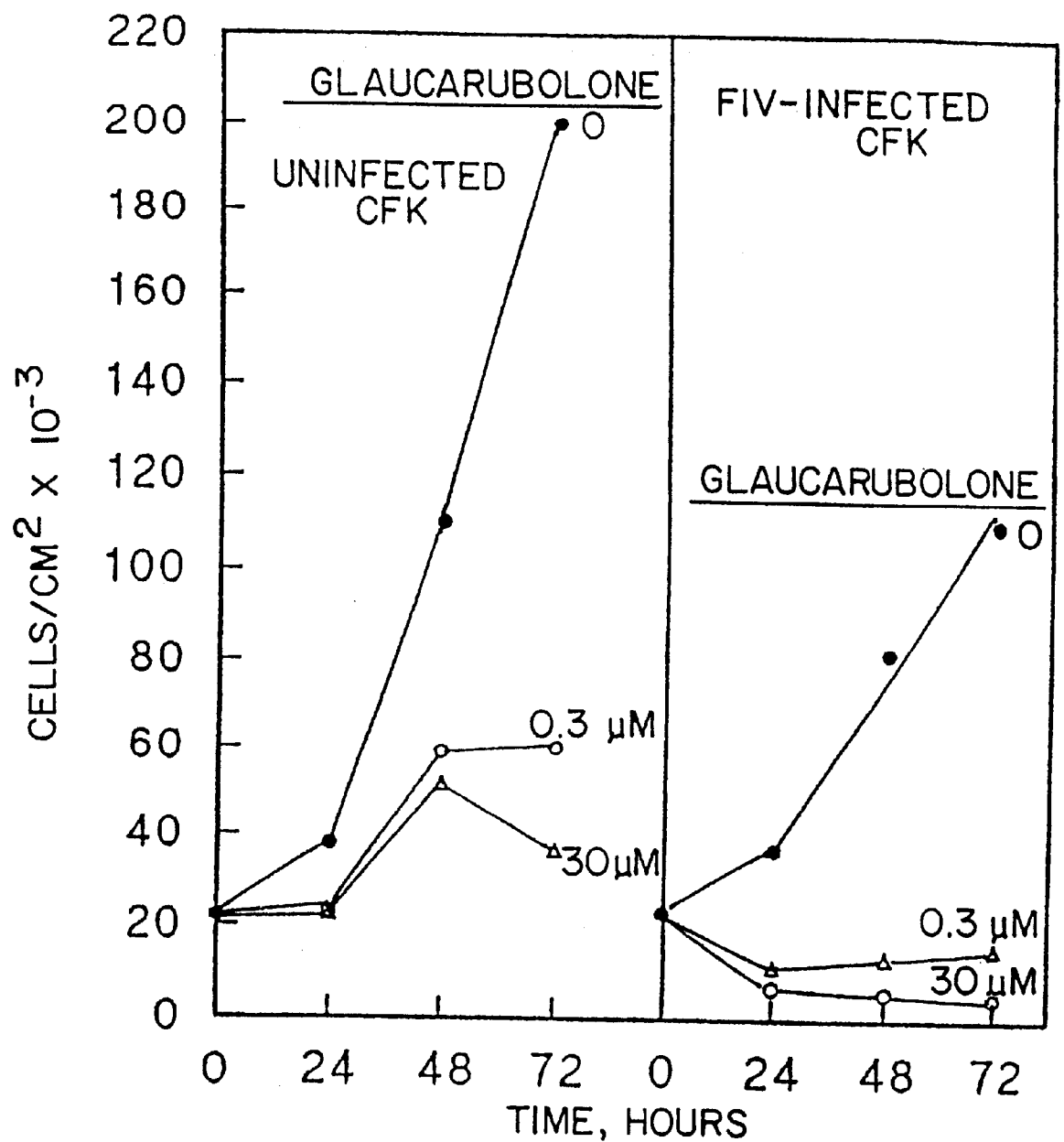
FIG. 7 is a graph comparing cell concentration against time for feline immunodeficiency virus (FIV) infected and control Crandall Feline Kidney cells contacted with glaucarubolone.

A. Crandall Feline Kidney cells (CFK cells) were infected with Feline Immunodeficiency Virus (FIV) and examined with glaucarubolone and glaucarubolone-brefeldin A conjugate such as seen in FIG. 6. As seen in FIGS. 6 and 7, and Table 3 hereinafter, both exhibited differential killing of infected cells as compared to non-infected cells.

Figure 8:
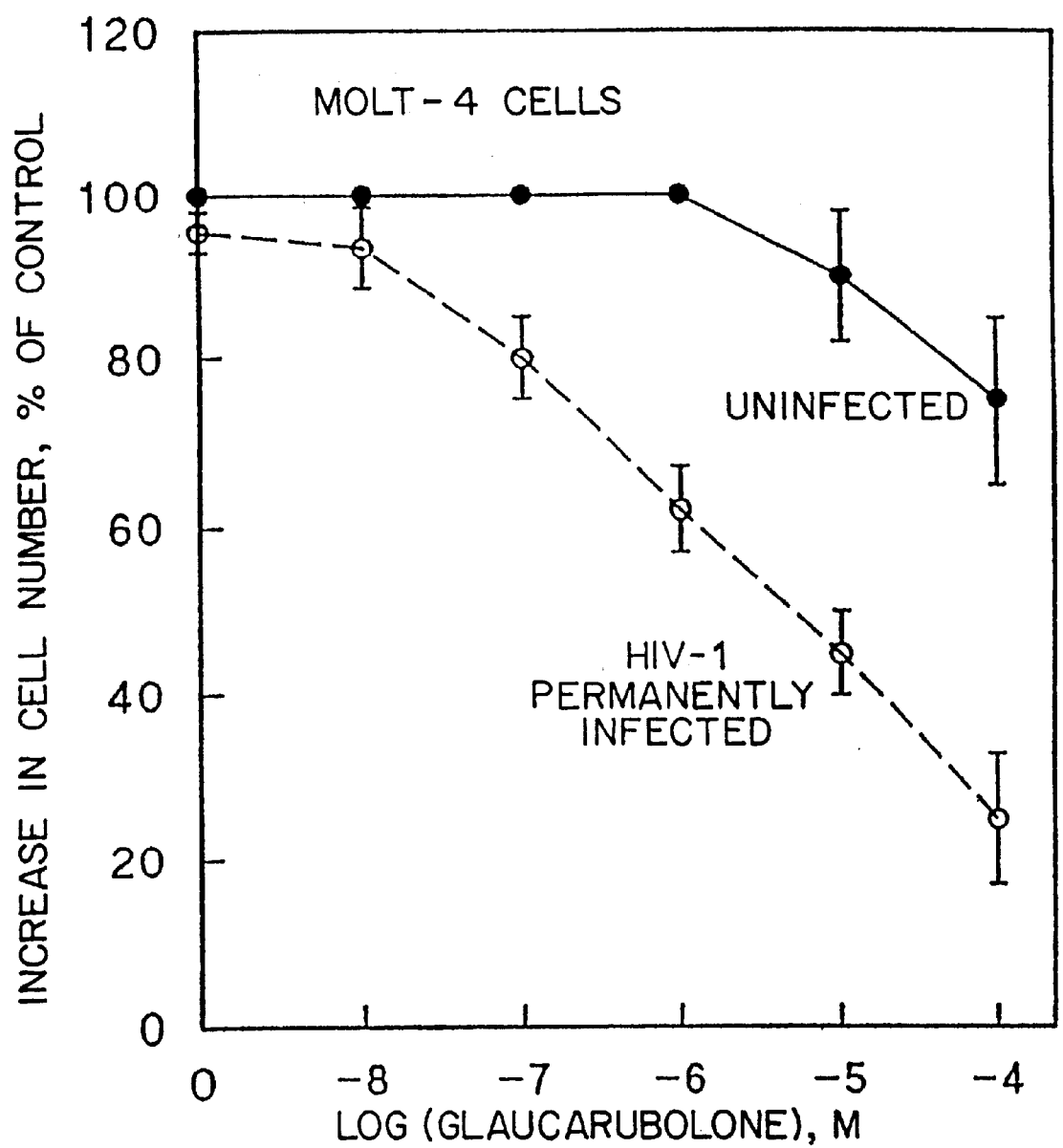
FIG. 8 is a graph comparing log concentration of glaucarubolone to the increase in cell number of human immunodeficiency virus (HIV) infected cells and uninfected control cells.
Figure 9:
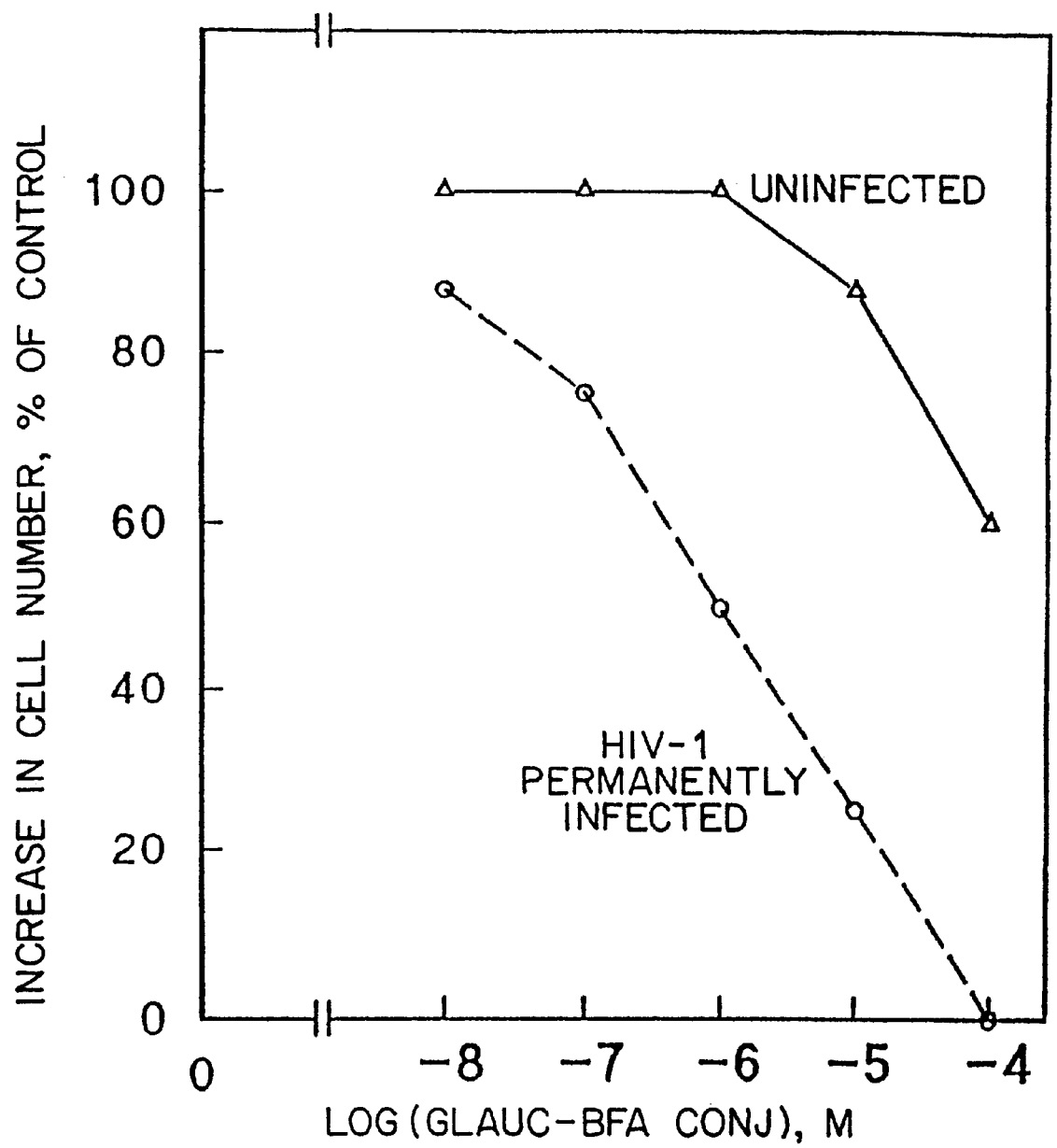
FIG. 9 is a graph comparing log concentration of a glaucarubolone-brefeldin A conjugate to the increase in cell number of human immunodeficiency virus (HIV) infected cells and uninfected control cells.

B. As seen in FIG. 8, HIV infected human MOLT-4 cells were differentially killed at two log orders less of glaucarubolone than uninfected cells. As seen in FIG. 9, similar activity was observed with a glaucarubolone-brefeldin A conjugate. C. HeLa cells (Wisconsin strain, Berlin, Germany) were contacted with human rhinovirus-14. Infected cells (Wisconsin strain) were visually observed. Cytopathic effect was delayed by glaucarubolone, simalikalactone D, quassimarine, and peninsularinone. HeLa cells were not killed by any compounds used. Cells of other HeLa lines (eg. ATCC CCL2) were killed. Glaucarubolone, simalikalactone D and chaparrinone were tested on cell killing and virus production by primary blood monocytes. All three drugs were tested at five concentrations (0, $10^{-9}$, $10^{-8}$, $10^{-7}$, and $10^{-6}$ M). Drugs were given at different times pre-infection, given at the time of infection, or were administered at different times post-infection. Equivalent results were obtained, suggesting that the toxicity effects were against the infected cells rather than the virus per se.

D. Rabbit kidney cells were contacted with porcine pseudorabies virus and visually monitored. Glaucarubolone inhibited cytopathic effect of the virus and exhibited no cytopathic affect on non-infected glaucarubolone treated control cells. Inhibitory effect was also observed with quassimarine, similakalactone D, bruceantin, and peninsularinone.

Figure 10:
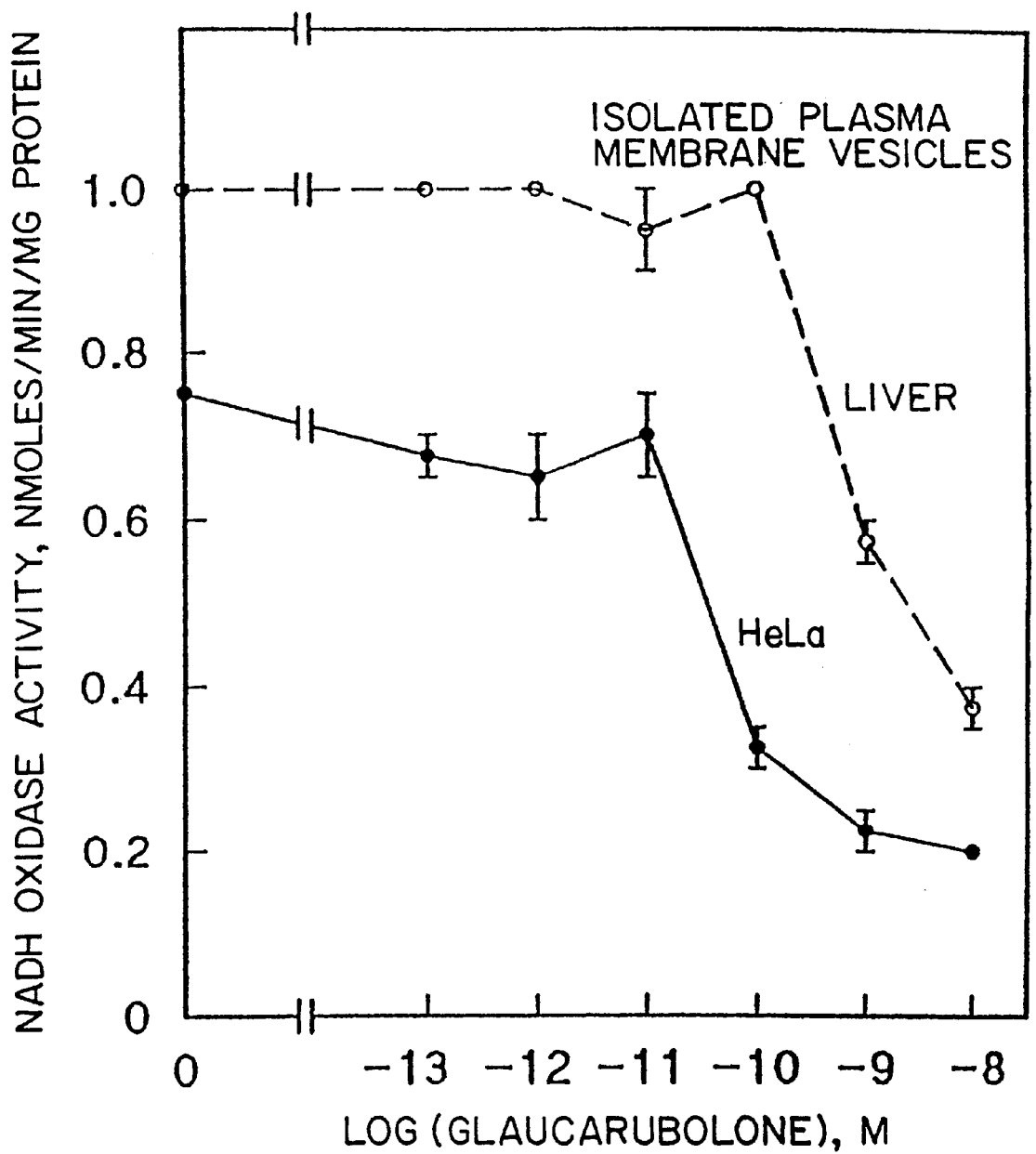
FIG. 10 is a graph showing glaucarubolone inhibition of NADH oxidation in both HeLA and isolated plasma membranes of liver cells.
Figure 11:
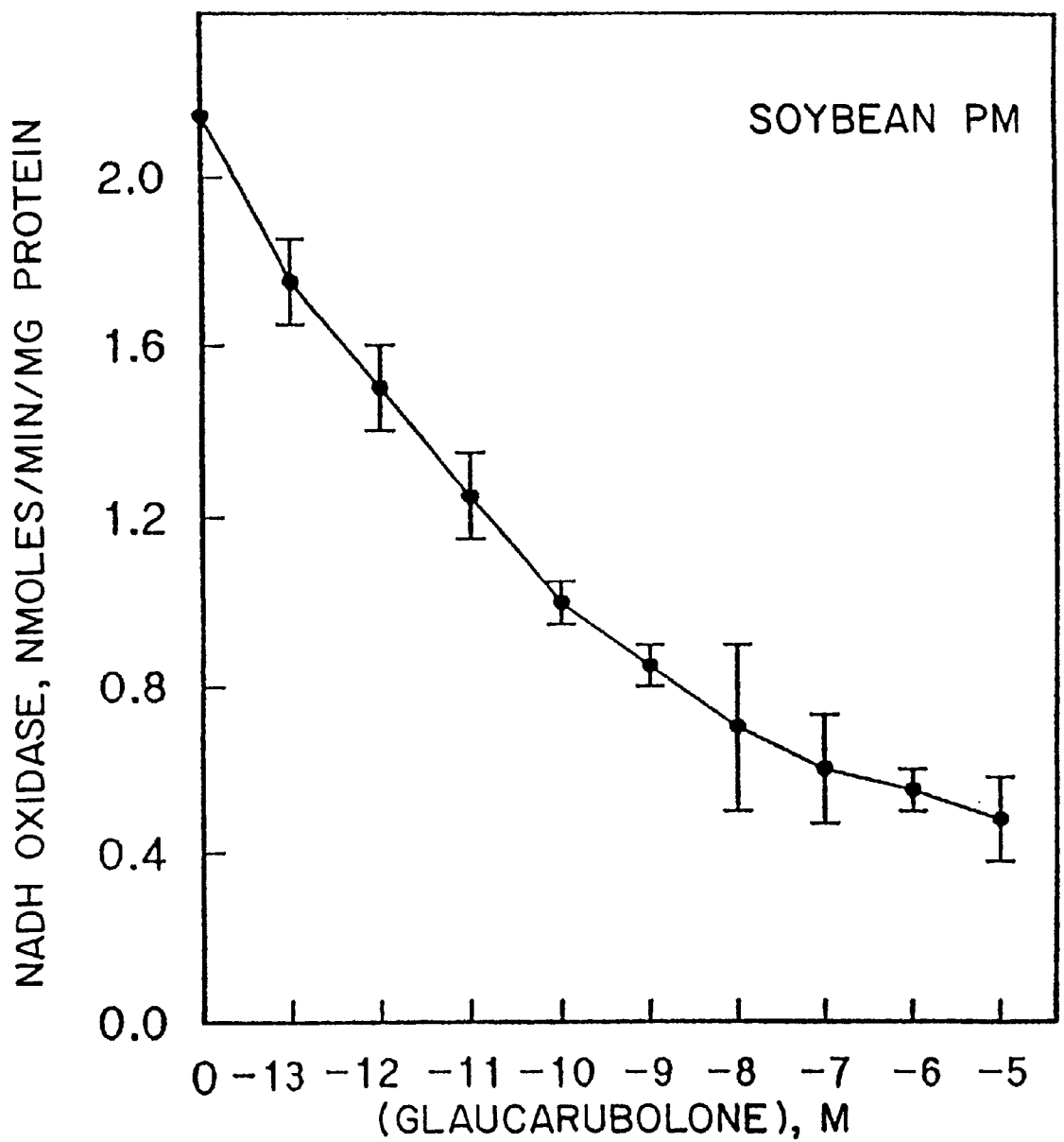
FIG. 11 indicates inhibition of NADH oxidation in plant soybean cells treated with glaucarubolone.

E. Inhibition of NADH oxidase activity in animal and plant cells is indicated with reference to Table 4 and FIGS. 10 and 11. Glaucarubolone is found to inhibit plasma membrane NADH oxidation in feline immunodeficiency virus infected HeLa cells, as well as non-infected cells. As seen in FIG. 10, glaucarubolone inhibits NADH oxidation in both HeLa (ATCC CCL2 strain) and isolated plasma membranes of liver cells. As seen in FIG. 11, NADH oxidation is similarly inhibited in plant soybean hypocotyl tissue.

TABLE 3

Time for complete cell killing (>98%) by glaucarubolone

| | Hr | |
|---|---|---|
| Glaucarubolone, M | Uninfected | FIV-Infected |
| $3 \times 10^{-4}$ | 120 | >168 |
| $3 \times 10^{-5}$ | 120 | >168 |
| $3 \times 10^{-6}$ | 144 | >168 |
| $3 \times 10^{-7}$ | 192 | >168 |
| $3 \times 10^{-8}$ | >192 | >168 |
| $3 \times 10^{-9}$ | >192 | >168 |

TABLE 4

Glaucarubolone inhibition of NADH oxidase activity of cell fractions

| Cell Fraction | $ED_{50}$ |
|---|---|
| Rat liver golgi apparatus | $>10^{-5}$ M |
| Rat liver microsomes | $>10^{-5}$ M |
| Rat lkiver plasma membrane | $>10^{-5}$ M |
| Plasma membrane-free CFK microsomes (Golgi-enriched) from uninfected cells | $>10^{-5}$ M |
| Plasma membrane-free CFK microsomes (Golgi-enriched) from infected cells | $>10^{-8}$ M |

TABLE 5

Inhibition by varying concentrations of simalikakactone D of NADH oxidase activity of isolated plasma membrane vesicles isolated from elongating sections of dark-grown soybean hypocotyls and of growth of 1 cm sections cut from the elongating zone of dark-grown soybean hypocotyls and floated on solution. The inhibition of the NADH oxidase was determined by adding the simalikalactone D solutions directly to the isolated plasma membrane vesicles.

| Parameter | $ED_{50}$ |
|---|---|
| Inhibition of NADH oxidase[1] | 0.4 µM |
| Inhibition of 2,4-D (1 µM)-induced growth[2] | 3.5 µM |
| Inhibition of control growth[2] | 2.5 µM |

[1]Isolated PM vesicles
[2]Excised segments of etiolated soybean hypocotyls (18 h)

EXAMPLE 5

Herbistatic and Herbicidal Activity

Compounds according to the present invention have been found to affect the growth phenotype of plants, typically by inhibiting continued growth of plants or causing plant cell death. The present invention therefore comprises utilization of quassinoids such as glaucarubolone as herbistats or herbicides, useful in conjunction with conventional herbistatic of herbicidal carriers known to those skilled in the art to control plant growth. The mechanism of herbistatic and herbicidal action is believed to rely on modifications of cellular NADH oxidase activity. Uniquely, inhibition of both basal and the auxin-stimulated component of NADH oxidase in plants were identified.

To evaluate the growth phenotype of a set of plats, a 1 mg sample of glaucarubolone was dissolved in DMSO or ethanol at a final concentration of 100 Mm (solution QD-2). This solution was diluted serially with water with or without Triton X-100, ethanol or DMSO and used directly for measurement of effects on seed germination or applied using a microliter syringe to foliage to evaluate growth effects on plants.

With seed germination, the compound was evaluated against five species: cabbage (Early Jersey Wakefield), radish (Scarlet Turnip White Tipped), carrot (Danvers Half Long), tomato (Rutgers) and sorghum (DeKalb 18). With water dilutions, seed germination of all species was inhibited at 10 $\mu$M (an aqueous dilution of 10 $\mu$l of 100 Mm 1:1000 in 100 $\mu$l of water) (Final DMSO concentration of 1:10,000=0.01%). Germination of tomato was inhibited at 10$\mu$l/100$\mu$l of an aqueous dilution of 1:10,000=1 $\mu$M final concentration. With DMSO and ethanol dilutions, inhibitions were observed at final dilutions as low as 1:10$^8$ or 1:10$^7$ (10–100 Nm) but the solvents themselves tended to retard the germination as well.

When applied to Arabadopsis (var. Columbia) growing in soil in 4 inch plastic pots, the glaucarubolone preparation was herbicidal at dilutions of 1:100 and 1:1000 (10$\mu$l/half pot). Plants were treated after 10 days of germination. At a dilution of 1:10,000, the plants were not killed but growth was completely stopped for about 3 weeks. Growth resumed about 30 days after treatment. The application rate to the treated area (estimated to be a 2 inch diameter circle) was calculated to be 2.5×10$^{-4}$ oz/A. Approximately 10% of the plants which survived a dilution of 1:1000 did not grow for >50 days. The calculated application rate was 2.5×10$^{-3}$ oz/A.

Sorghum (DeKalb 18) plants growing in soil were treated as for *Arabadopsis thaliani* above after 6 days of germination when the plants were about 5 cm high (as the leaf emerged from the coleoptile sheath). Growth was retarded. Twenty days after treatment, control plants were 16 cm high and treated plants were 12 cm high. The application rate was 10$\mu$l of 1:1000/half pot=2.5×10$^{-3}$ oz/A.

Tomato plants about 3.5 cm high at the time of treatment were grown in peat in a flat of 1.5 inch diameter compartments and were treated with either aqueous simalikalactone (solution QD-1) or aqueous glaucarubolone (solution QD-2) containing 0.1% Triton X-100. The final volume/plant was 10$\mu$l for the aqueous solution and 200$\mu$l of the aqueous solution containing Triton X-100. At an application rate of 100 Mm diluted 1:100 (10$\mu$l in 200$\mu$l of 0.1% Triton X-100), the treated plants did not grow and eventually died after about 30 days. At 30 days after treatment, the treated plants receiving 1:1000 and 1:10,000 dilutions in detergent solution were still inhibited. With the aqueous treatment, plants also were inhibited but not as markedly as with detergent.

In an experiment with Arabadopsis where the quassinoid preparation was administered in ethanol, herbicidal activity was observed down to a dilution of 1:10$^4$ (2.5×10$^{-5}$ oz/A) and a dilution of 1:10$^5$ (2.5×10$^{-6}$ oz/A) appeared to stop growth for at least 30 days. All plants were watered from the bottom to reduce surface spreading of the material. The inhibited phenotype includes an impaired ability of the plants to grow, i.e., cell elongation/cell expansion is prevented or reduced by at least 50% over several weeks.

EXAMPLE 6

The Preparation of Anticancer Drug Conjugates Involving Quassinoids Targeted Specifically to a Cell Surface NADH Oxidase Specific to Cancer Cells and Designated as tNOX The drug site for tNOX is located at the external surface of the cancer cells. As such, the drug need not enter the cell to be effective. In fact, one purpose of the conjugates here described is to reduce toxicity by preventing entry of the drug into cells.

The growth of cells, preparation of plasma membranes and spectrophotometric measurements were performed as described hereinabove.

During preliminary studies a derivatized glaucarubolone (below) was prepared for conjugation with antibodies. The derivatized drug was coupled to amino propyleneglycol (Ave MW 5000) in the presence of 10 mM of the coupling reagent dicyclohexylcarbodiimide (DCC) (Sigma).

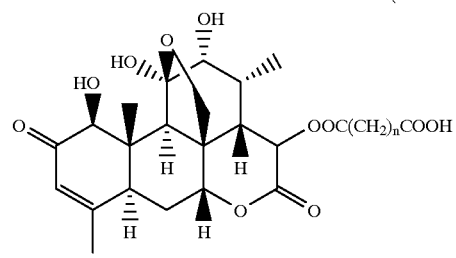

(Formula XIV)

This embodiment is the basis for a new strategy of anticancer drug design where anticancer quassinoids targeted to tNOX are combined with polymers to enhance efficacy and reduce unwanted toxicities. The conjugated drugs need not enter cells to be effective and can be targeted specifically to cells carrying specific determinants. The invention is an improvement over what now exists because it provides a cell surface target and a high degree of specificity. Accordingly, drugs need not enter the cell to be effective. By targeting specifically to cancer cells, only cancer cells are killed and normal cells remain unharmed.

The small molecule entity made impermeant by polymer conjugation can include any quassinoid tNOX inhibitor, including but not restricted to glaucarubolone. The polymers can include any water soluble appropriately fractionalized macromolecule, including but not restricted to proteins, dextrans, cyclodextrins, polyethyleneglycols, nucleic acids, polymers of ethylene- or propyleneglycol and various simple and complex carbohydrate polymers. Polymer characteristics appropriate to preparation of effective anti-tNOX drug-conjugates for use in cancer management include a high degree of water solubility, low toxicity and low antigenicity. Cyclodextrins, polyethyleneglycols and the ethylene- or propyleneoxide polymers exhibit nearly ideal characteristics in this regard. The number of polymer subunits may vary from n=1 to n=1000 or higher depending on the solubility and permeation characteristics required to optimize delivery of drug to the target site. In the simplest example where n=1, the drug would be conjugated only to ensure delivery to the tNOX target and to restrict cell entry, but not to limit entry of the drug into solid tumors and tumor cell aggregates, thereby precluding development of a conjugate with good oral bioavailability. Linkage of small molecules and polymers may be accomplished in various ways including but not restricted to the examples given above. Factors important to the linkage method would include ease of manufacture, reproducibility and relative conjugate stability.

Figure 12:
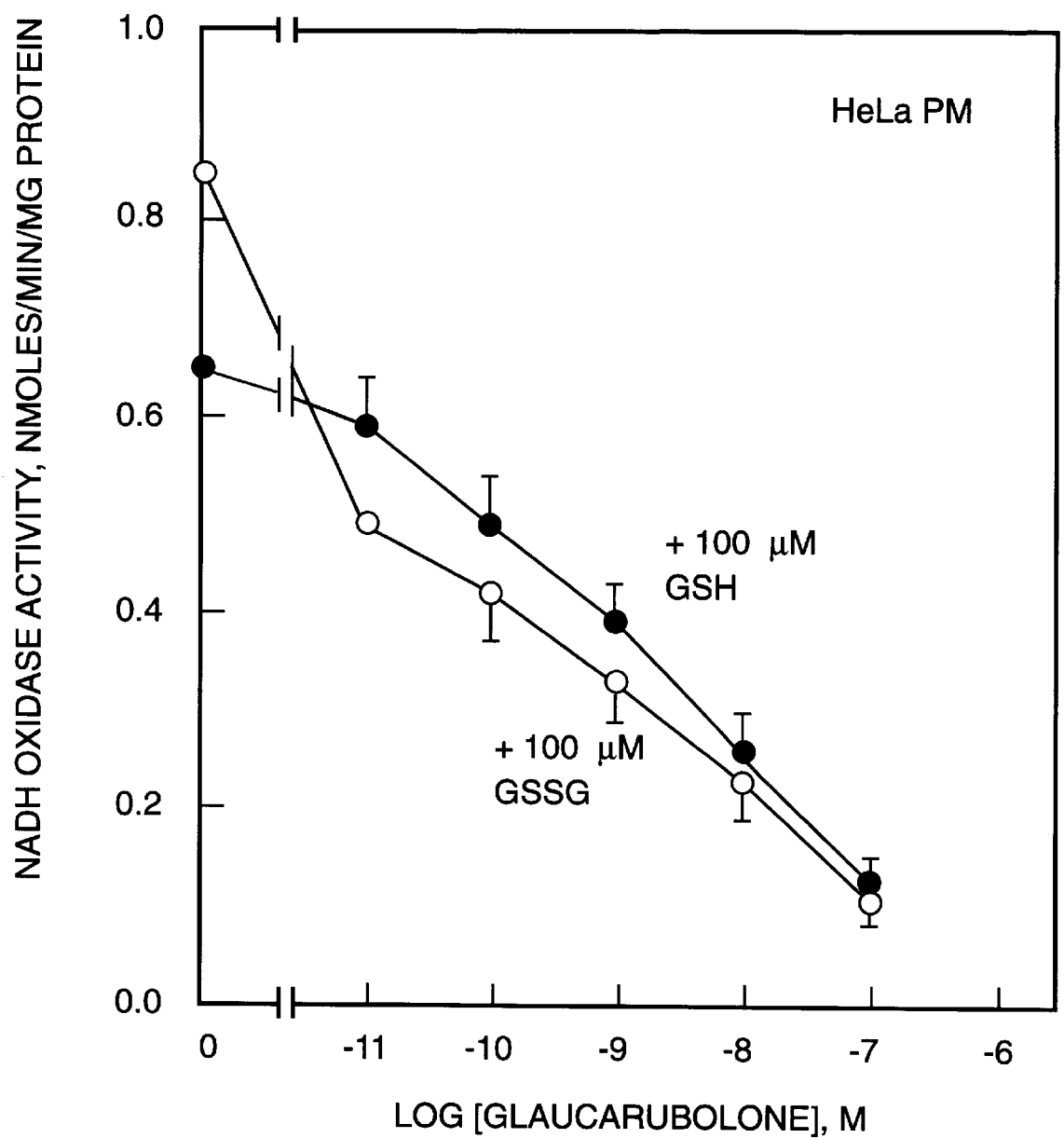
FIG. 12 is a graph showing the effect of redox poise on glaucarubolone inhibition of NADH oxidation in HeLa cell plasma membranes.
Figure 13:
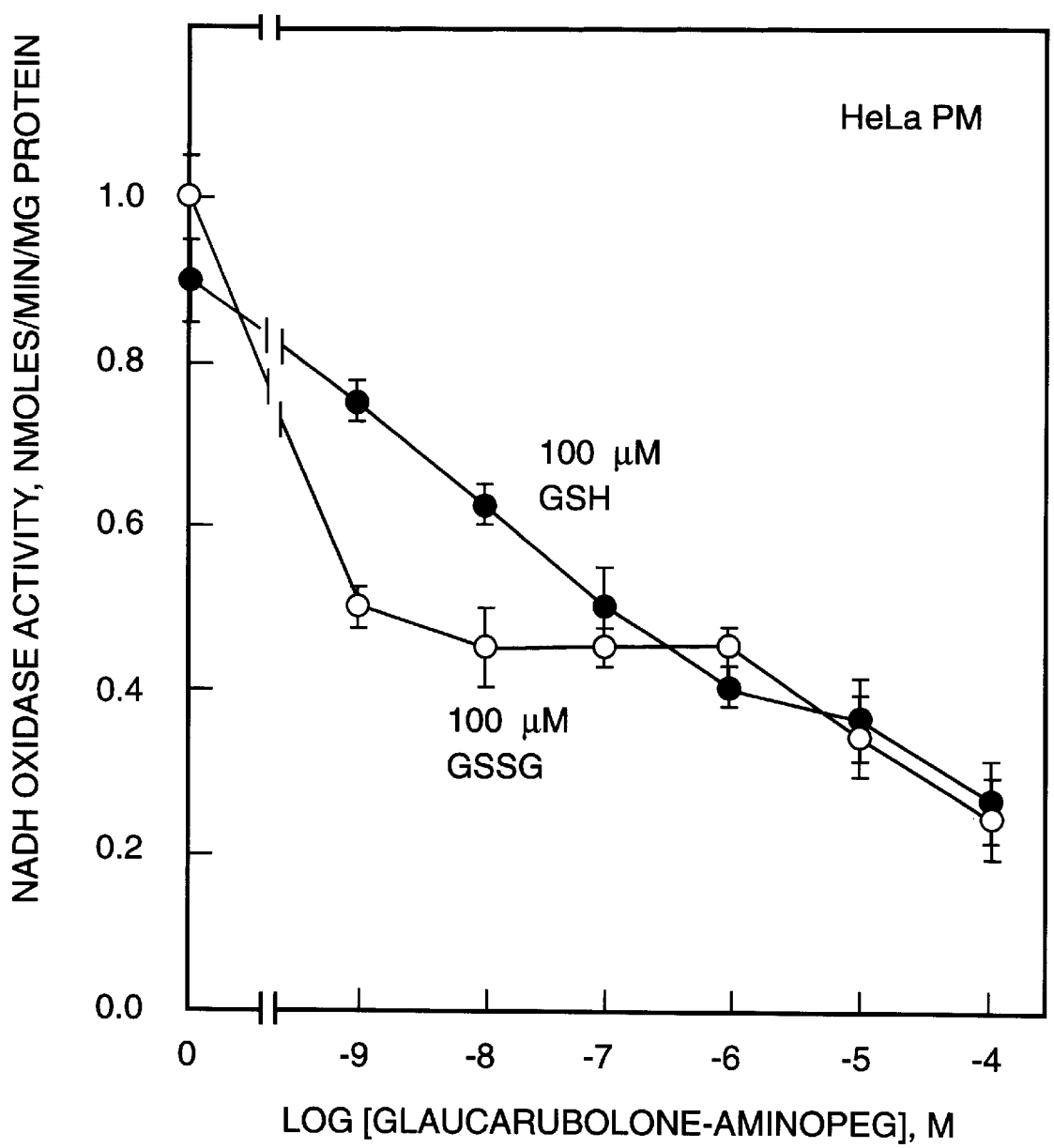
FIG. 13 is a graph showing the inhibition of NADH oxidase activity of HeLa cell plasma membranes by a glaucarubolone-amino polyethyleneglycol drug conjugate.

As seen in FIG. 12, the dependence of NADH oxidase activity of HeLa cell plasma membranes on the concentration of glaucarubolone is affected little by redox poise. It appears to represent a redox poise-independent tNOX inhibitor. Further, as seen in FIG. 13, the glaucarubolone-amino polyethyleneglycol drug conjugate appears to inhibit the constitutively-activated tNOX activity at subnanomolar concentrations in the presence of GSSG oxidized at 1 µM in the presence of GSH.

Table 6 shows the redox independence of the inhibition of growth of HeLa cells by the glaucarubolone-amino polyethyleneglycol conjugate compared to glaucarubolone alone. The reduced environment was obtained by addition of 100 µM cysteine and the oxidized environment by addition of 10 µM tert-butylhydroperoxide.

TABLE 6

Growth of HeLa cells after 72 h.

| Treatment | Reduced | In situ (cells/mm²) | Oxidized |
|---|---|---|---|
| No drug | 725 | 725 | 725 |
| Glaucarbolone $10^{-7}$ M | 700 | 720 | 500 |
| Glaucarubolone-AminoPEG conj. $10^{-7}$ M | 480 | 530 | 270 |
| Glaucarubolone-AminoPEG conj. $10^{-6}$ M | 50 | 50 | 30 |

Table 7 shows the response of normal and persistently infected CFK cells to glaucarubolone-aminoPEG conjugate tested at $10^{-6}$ M.

TABLE 7

| | | Cells/mm² | | |
|---|---|---|---|---|
| Cell line | Conjugate | Initial | After 48 h | Increase |
| Normal | None | 27 | 67 | 40 |
| | $10^{-6}$ | 26 | 73 | 45 |
| Persistently FIV-infected (Transformed) | None | 27 | 43 | 16 |
| | $10^{-6}$ M | 20 | 9 | -11 |

While the present invention has been described in connection with specific embodiments, it will be apparent to those skilled in the art that various changes may be made therein without departing from the spirit or scope of the invention.

The claimed invention is:
1. A compound characterized by the formula

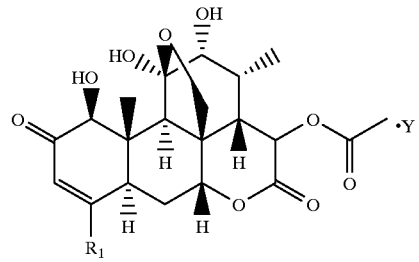

wherein $R_1$ represents hydrogen, oxygen, alkyl, alkenyl, acyl, aryl, halogen, sulfo, nitro, carboxyl, hydroxyl, hydroxyalkyl, alkoxy, or water soluble sidechain, and Y is a sidechain comprising hydrogen, alkyl (excluding holocanthone, castelanone and ailanthinone), hydroxyalkyl (excluding soularubinone and glaucarubinone), carboxyl (excluding glaucarubinone-2'-acetate), substituted aryl, alkenyl, cycloalkanes, cycloalkenes, glycosaccharides, water soluble sidechains selected from the group consisting of:

dextrans, dextrins, cyclodextrins, polyethyleneglycols, polymers of ethyleneglycol, polymers of propyleneglycol, carbohydrate polymers, carboxymethylcellulose, polyamines, polyglutamine, N-(2-hydroxypropyl)methacrylamide copolymers, polyoxamines, polyoxyethylene block polymers, and polyoxypropylene block polymers, amino acid, peptide, polypeptide, protein selected from the group consisting of: antibodies, immunoglobulins, growth hormones, interferons, plasma albumin, plasminogen activator, soybean trypsin inhibitor, L-asparaginase, and ribonuclease, and any of the foregoing attached by an ether, ester, carbonyl, or glycosidic linkage.

2. A therapeutic composition for treatment of viral diseases comprising a combination of a compound characterized by the formula

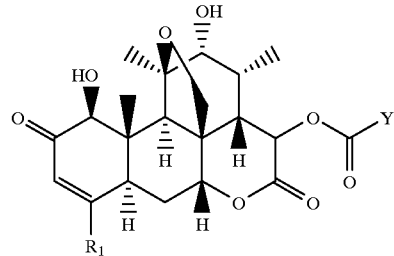

wherein $R_1$ represents hydrogen, oxygen, alkyl, alkenyl, acyl, aryl, halogen, sulfo, nitro, carboxyl, hydroxyl, hydroxyalkyl, alkoxy, or other water soluble sidechain, and Y is a sidechain comprising hydrogen, alkyl, hydroxyalkyl, carboxyl, aryl, alkenyl, cycloalkanes, cycloalkenes, glycine, glycosaccharides, water soluble sidechains selected from the group consisting of:

dextrans, dextrins, cyclodextrins, polyethyleneglycols, polymers of ethyleneglycol, polymers of propyleneglycol, carbohydrate polymers, carboxymethylcellulose, polyamines, polyglutamine, N-(2-hydroxypropyl)methacrylamide copolymers, polyoxamines, polyoxyethylene block polymers, and polyoxypropylene block polymers, amino acid, peptide, polypeptide, lipids, nucleic acids, derivatized polymeric substances, naturally occurring macromolecules, protein selected from the group consisting of: antibodies, immunoglobulins, growth hormones, interferons, plasma albumin, plasminogen activator, soybean trypsin inhibitor, L-asparaginase, and ribonuclease, and any of the foregoing attached to the C-15 carbon by an ether, ester, carbonyl, or glycosidic linkage and a pharmaceutically acceptable carrier therefor.

3. A therapeutic preparation comprising a pharmaceutically effective carrier and a compound represented by the formula

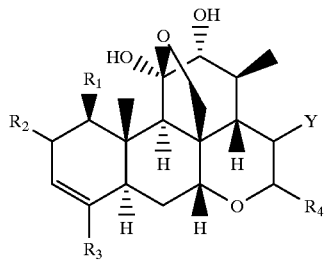

wherein $R_1$ represents a hydroxyl, $R_2$ and $R_4$ represent double bonded oxygen, $R_3$ represents hydrogen, oxygen, alkyl, alkenyl, acyl, aryl, halogen, sulfo, nitro, carboxyl, hydroxyl, hydroxyalkyl, alkoxy, or other water soluble sidechain, and Y is a sidechain comprising hydrogen, oxygen, halogen, hydroxyl, ester, carbonyl, alkyl, hydroxyalkyl, aryl, glycine, glycosaccharides, water soluble sidechains selected from the group consisting of:

dextrans, dextrins cyclodextrins, polyethyleneglycols, polymers of ethyleneglycol, polymers of propyleneglycol, carbohydrate polymers, carboxymethylcellulose, polyamines, polyglutamine, N-(2-hydroxypropyl)methacrylamide copolymers, polyoxamines, polyoxyethylene block polymers, and polyoxypropylene block polymers, amino acid, peptide, polypeptide, lipids, nucleic acids, derivatized polymeric substances, naturally occurring macromolecules, protein selected from the group consisting of: antibodies, immunoglobulins, growth hormones, interferons, plasma albumin, plasminogen activator, soybean trypsin inhibitor, L-asparaginase and ribonuclease, and any of the foregoing attached to the C-15 carbon by an ether, ester, carbonyl, or glycosidic linkage.

4. A method for inhibiting plant growth comprising the steps of preparing a herbistat composition containing a quassinoid represented by the formula

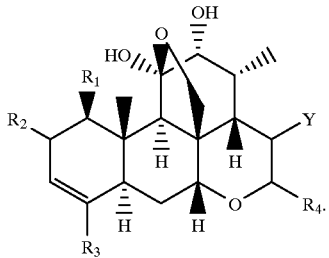

wherein $R_1$ represents a hydroxyl, $R_2$ and $R_4$ represent double bonded oxygen, $R_3$ represents hydrogen, oxygen, alkyl, alkenyl, acyl, aryl, halogen, sulfo, nitro, carboxyl, hydroxyl, hydroxyalkyl, alkoxy, or other water soluble sidechain, and Y is a sidechain comprising hydrogen, oxygen, halogen, hydroxyl, ester, carbonyl, alkyl, hydroxyalkyl, aryl, glycine, glycosaccharides, water soluble sidechains, amino acid, peptide, polypeptide, lipids, nucleic acids, derivatized polymeric substances, naturally occurring macromolecules, protein, and any of the foregoing attached to the C-15 carbon by an ether, ester, carbonyl, or glycosidic linkage, and contacting plants with said herbistatic composition to control plant growth rate.

5. A method according to claim 4, wherein Y represents a hydroxyl group.

6. A method for inhibiting plant growth comprising the steps of preparing a herbistat composition containing a quassinoid represented by the formula

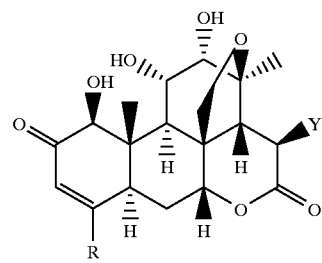

wherein R represents hydrogen, oxygen, alkyl, alkenyl, acyl, aryl, halogen, sulfo, nitro, carboxyl, hydroxyl, hydroxyalkyl, alkoxy, or other water soluble sidechain, and Y is a sidechain comprising hydrogen, oxygen, halogen, hydroxyl, ester, carbonyl, alkyl, hydroxyalkyl, aryl, glycine, glycosaccharides, water soluble sidechains, amino acid, peptide, polypeptide, lipids, nucleic acids, derivatized polymeric substances, naturally occurring macromolecules, protein, and any of the foregoing attached to the C-15 carbon by an ether, ester, carbonyl, or glycosidic linkage and contacting plants with said herbistatic composition to control plant growth rate.

7. A method according to claim 6 wherein Y comprises an ester sidechain represented by the formula

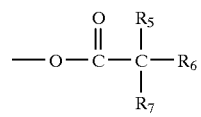

wherein $R_5$, $R_6$, and $R_7$ represent hydrogen, halogen, methyl, ethyl, alkyl, aryl, hydroxyl, carboxyl, glycine, glycosaccharides, water soluble sidechains, amino acid, peptide, polypeptide, protein, and any of the foregoing attached to the central carbon by an ether, ester, carbonyl, or glycosidic linkage.

8. A method according to claim 7, wherein $R_5$ represents a methyl group, $R_6$ represents hydrogen, and $R_7$ represents an ethyl group.

9. A method for treating solid tumors comprising the steps of preparing a pharmaceutically active composition containing a quassinoid represented by the formula

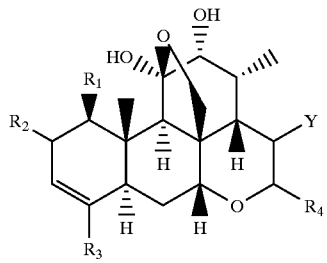

wherein $R_1$ represents a hydroxyl, $R_2$ and $R_4$ represent double bonded oxygen, $R_3$ represents hydrogen, oxygen, alkyl, alkenyl, acyl, aryl, halogen, sulfo, nitro, carboxyl, hydroxyl, hydroxyalkyl, alkoxy, or other water soluble sidechain, and Y is a sidechain comprising hydrogen, oxygen, halogen, hydroxyl, ester, carbonyl, alkyl, hydroxyalkyl, aryl, glycine, glycosaccharides, water soluble sidechains, amino acid, peptide, polypeptide, lipids, nucleic acids, derivatized polymeric substances, naturally occurring macromolecules, protein, and any of the foregoing attached to the C-15 carbon by an ether, ester, carbonyl, or glycosidic linkage, and contacting the solid tumors with said pharmaceutically active composition.

10. The method of claim 9 wherein Y includes a water soluble sidechain selected from the group consisting of:

dextrans, dextrins, cyclodextrins, polyethyleneglycols, polymers of ethyleneglycol, polymers of propyleneglycol, carbohydrate polymers, carboxymethylcellulose, polyamines, polyglutamine, N-(2-hydroxypropyl)methacrylamide copolymers, polyoxamines, polyoxyethylene block polymers, and polyoxypropylene block polymers.

11. A method according to claim 9 wherein Y comprises an ester sidechain represented by the formula

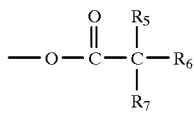

wherein $R_5$, $R_6$, and $R_7$ represent hydrogen, halogen, methyl, ethyl, alkyl, aryl, hydroxyl, carboxyl, glycine, glycosaccharides, water soluble sidechains, amino acid, peptide, polypeptide, protein, and any of the foregoing attached to the central carbon by an ether, ester, carbonyl, or glycosidic linkage.

12. A method according to claim 11, wherein $R_5$ represents a methyl group, $R_6$ represents an ethyl group, and $R_7$ represents a hydroxyl group.

13. A method according to claim 11, wherein $R_5$, $R_6$, and $R_7$ each represent hydrogen.

14. A method according to claim 9, wherein Y represents a hydroxyl group.

15. A method according to claim 9, wherein Y represents hydrogen.

16. A method according to claim 9 wherein Y comprises an ester sidechain represented by the formula

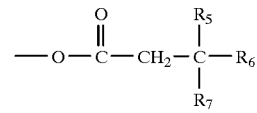

wherein $R_5$, $R_6$, and $R_7$ represent hydrogen, halogen, methyl, ethyl, alkyl, aryl, hydroxyl, carboxyl, glycine, glycosaccharides, water soluble sidechains, amino acid, peptide, polypeptide, protein, and any of the foregoing attached to the central carbon by an ether, ester, carbonyl, or glycosidic linkage.

17. A method according to claim 16, wherein $R_5$ represents an ethyl group, $R_6$ represents an ethyl group, and $R_7$ represents a hydroxyl group.

18. A method for treating solid tumors comprising the steps of preparing a pharmaceutically active composition containing a quassinoid represented by the formula

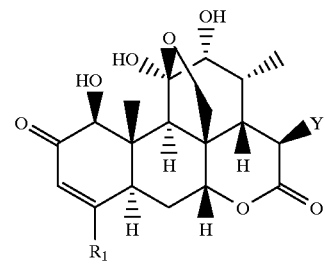

wherein $R_1$ represents hydrogen, oxygen, alkyl, alkenyl, acyl, aryl, halogen, sulfo, nitro, carboxyl, hydroxyl, hydroxyalkyl, alkoxy, or other water soluble sidechain, and Y is a sidechain comprising hydrogen, alkyl, hydroxyalkyl, carboxyl, aryl, alkenyl, cycloalkanes, cycloalkenes, glycine, glycosaccharides, water soluble sidechains selected from the group consisting of:

dextrans, dextrins, cyclodextrins, polyethyleneglycols, polymers of ethyleneglycol, polymers of propyleneglycol, carbohydrate polymers, carboxymethylcellulose, polyamines, polyglutamine, N-(2-hydroxypropyl)methacrylamide copolymers, polyoxamines, polyoxyethylene block polymers, and polyoxypropylene block polymers, amino acid, peptide, polypeptide, lipids, nucleic acids, derivatized polymeric substances, naturally occurring macromolecules, protein selected from the group consisting of: antibodies, immunoglobulins, growth hormones, interferons, plasma albumin, plasminogen activator, soybean trypsin inhibitor, L-asparaginase, and ribonuclease, and any of the foregoing attached to the C-15 carbon by an ether, ester, carbonyl, or glycosidic linkage and contacting the solid tumors with said pharmaceutically active composition.

19. A compound characterized by the formula

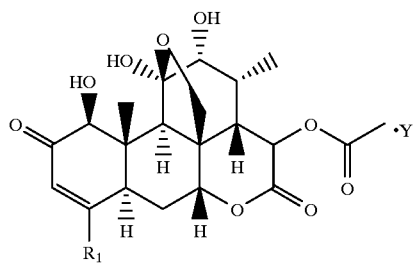

wherein $R_1$ represents hydrogen, oxygen, an alkyl having at least two carbons, alkenyl, acyl, aryl, halogen, sulfo, nitro, carboxyl, hydroxyl, hydroxyalkyl, alkoxy, or other water soluble sidechain, and Y is a sidechain comprising hydrogen, alkyl, hydroxyalkyl, carboxyl, aryl, alkenyl, cycloalkanes, cycloalkenes, glycosaccharides, water soluble sidechains, amino acid, peptide, polypeptide, protein, and any of the foregoing attached by an ether, ester, carbonyl, or glycosidic linkage.

20. The compound of claim 19 wherein Y includes a water soluble sidechain selected from the group consisting of:
dextrans, dextrins, cyclodextrins, polyethyleneglycols, polymers of ethyleneglycol, polymers of propyleneglycol, carbohydrate polymers, carboxymethylcellulose, polyamines, polyglutamine, N-(2-hydroxypropyl)methacrylamide copolymers, polyoxamines, polyoxyethylene block polymers, and polyoxypropylene block polymers.

21. A compound characterized by the formula

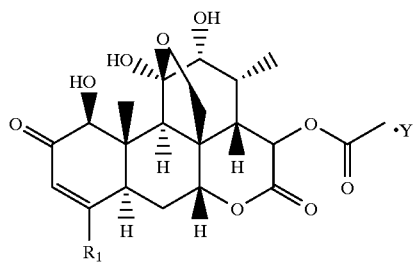

wherein $R_1$ represents hydrogen, oxygen, alkyl, alkenyl, acyl, aryl, halogen, sulfo, nitro, carboxyl, hydroxyl, hydroxyalkyl, alkoxy, or water soluble sidechain, and Y is a sidechain comprising hydrogen, carboxyl, aryl (excluding glaucarubolone-15-benzoate), cycloalkanes, cycloalkenes, glycosaccharides, water soluble sidechains, amino acid, peptide, polypeptide, protein, lipids, nucleic acids, derivatized polymeric substances, naturally occurring macromolecules, and any of the foregoing attached by an ether, ester, carbonyl, or glycosidic linkage.

22. The compound of claim 21 wherein Y includes a water soluble sidechain selected from the group consisting of:
dextrans, dextrins, cyclodextrins, polyethyleneglycols, polymers of ethyleneglycol, polymers of propyleneglycol, carbohydrate polymers, carboxymethylcellulose, polyamines, polyglutamine, N-(2-hydroxypropyl)methacrylamide copolymers, polyoxamines, polyoxyethylene block polymers, and polyoxypropylene block polymers.

23. The compound of claim 21 wherein Y includes a naturally occurring molecule selected from the group consisting of:
immunoglobulins, growth hormones, insulin, interferons, plasma albumin, fibrinogen, plasminogen activator, heparin, chondroitin sulfate, soybean trypsin inhibitor, L-asparaginase, and ribonuclease.

24. A compound characterized by the formula

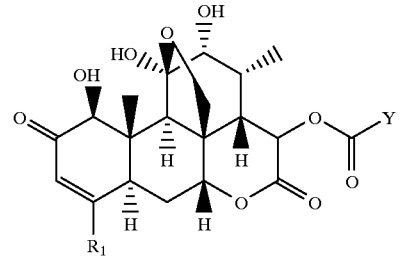

wherein $R_1$ represents hydrogen, oxygen, alkyl, alkenyl, acyl, aryl, halogen, sulfo, nitro, carboxyl, hydroxyl, hydroxyalkyl, alkoxy, or water soluble sidechain, and Y is a sidechain comprising hydrogen, alkyl, hydroxyalkyl, carboxyl, substituted aryl, alkenyl, cycloalkanes, cycloalkenes, glycosaccharides, water soluble sidechains selected from the group consisting of:
dextrans, dextrins, cyclodextrins, polyethyleneglycols, polymers of ethyleneglycol, polymers of propyleneglycol, carbohydrate polymers, carboxymethylcellulose, polyamines, polyglutamine, N-(2-hydroxypropyl) methacrylamide copolymers, polyoxamines, polyoxyethylene block polymers, and polyoxypropylene block polymers,
amino acid, peptide, polypeptide, lipids, nucleic acids, derivatized polymeric substances, naturally occurring macromolecules, protein selected from the group consisting of: antibodies, immunoglobulins, growth hormones, interferons, plasma albumin, plasminogen activator, soybean trypsin inhibitor, L-asparaginase, and ribonuclease,
and any of the foregoing attached to the C-15 carbon by an ether, ester, carbonyl, or glycosidic linkage, with the proviso that said compound is not ailanthinone, glaucarubinone, chaparrinone, glaucarubolone, castelanone, soularubinone, holacanthone, glaucarubolone-15-benzoate, 2'-acetylglaucarubinone, or glaucarubolone-15-tiglate, and with the further proviso that said Y is not a $C_5$ to $C_{18}$ 2-alkenoate or a $C_5$ to $C_{16}$ 3-methylalkenoate.

25. A therapeutic preparation comprising a pharmaceutically effective carrier and a compound represented by the formula

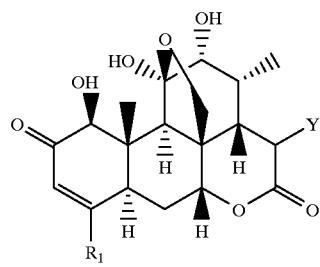

wherein $R_1$ represents hydrogen, oxygen, alkyl, alkenyl, acyl, aryl, halogen, sulfo, nitro, carboxyl, hydroxyl, hydroxyalkyl, alkoxy, or other water soluble sidechain, and Y is a sidechain comprising hydrogen, oxygen, halogen, hydroxyl, ester, carbonyl, alkyl, hydroxyalkyl, aryl, glycine, glycosaccharides, water soluble sidechains selected from the group consisting of:

dextrans, dextrins, cyclodextrins, polyethyleneglycols, polymers of ethyleneglycol, polymers of propyleneglycol, carbohydrate polymers, carboxymethylcellulose, polyamines, polyglutamine, N-(2-hydroxypropyl)methacrylamide copolymers, polyoxamines, polyoxyethylene block polymers, and polyoxypropylene block polymers, amino acid, peptide, polypeptide, lipids, nucleic acids, derivatized polymeric substances, naturally occurring macromolecules, protein selected from the group consisting of: antibodies, immunoglobulins, growth hormones, interferons, plasma albumin, plasminogen activator, soybean trypsin inhibitor, L-asparaginase, and ribonuclease, and any of the foregoing attached to the C-15 carbon by an ether, ester, carbonyl, or glycosidic linkage, with the proviso that said compound is not ailanthinone, glaucarubinone, chaparrinone, glaucarubolone, castelanone, soularubinone, holacanthone, glaucarubolone-15-benzoate, 2'-acetylglaurarubinone, or glaucarubolone-15-tiglate, and with the further proviso that said Y is not a $C_5$ to $C_{18}$ 2-alkenoate or a $C_5$ to $C_{16}$ 3-methylalkenoate.

26. A method for treating solid tumors comprising the steps of preparing a pharmaceutically active composition containing a quassinoid represented by the formula

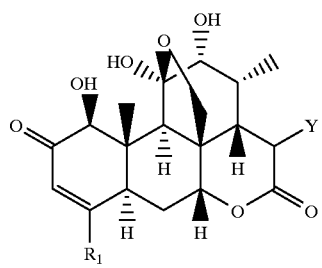

wherein $R_1$ represents hydrogen, oxygen, alkyl, alkenyl, acyl, aryl, halogen, sulfo, nitro, carboxyl, hydroxyl, hydroxyalkyl, alkoxy, or other water soluble sidechain, and Y is a sidechain comprising hydrogen, oxygen, halogen, hydroxyl, ester, carbonyl, alkyl, hydroxyalkyl, aryl, glycine, glycosaccharides, water soluble sidechains, amino acid, peptide, polypeptide, lipids, nucleic acids, derivatized polymeric substances, naturally occurring macromolecules, protein, and any of the foregoing attached to the C-15 carbon by an ether, ester, carbonyl, or glycosidic linkage, with the proviso that said quassinoid is not ailanthinone, glaucarubinone, chaparrinone, glaucarubolone, castelanone, soularubinone, holacanthone, glaucarubolone-15-benzoate, 2'-acetyglaucarubinone, or glaucarubolone-15-tiglate, and with the further proviso that said Y is not a $C_5$ to $C_{18}$ 2-alkenoate or a $C_5$ to $C_{16}$ 3-methylalkenoate, and contacting the solid tumors with said pharmaceutically active composition.

27. The method of claim 26 wherein Y includes a water soluble sidechain selected from the group consisting of:

dextrans, dextrins, cyclodextrins, polyethyleneglycols, polymers of ethyleneglycol, polymers of propyleneglycol, carbohydrate polymers, carboxymethylcellulose, polyamines, polyglutamine, N-(2-hydroxypropyl)methacrylamide copolymers, polyoxamines, polyoxyethylene block polymers, and polyoxypropylene block polymers.

28. A method according to claim 26 wherein Y comprises an ester sidechain represented by the formula

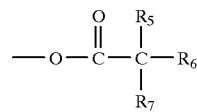

wherein $R_5$, $R_6$, and $R_7$ represent hydrogen, halogen, methyl, ethyl, alkyl, aryl, hydroxyl, carboxyl, glycine, glycosaccharides, water soluble sidechains, amino acid, peptide, polypeptide, protein, and any of the foregoing attached to the central carbon by an ether, ester, carbonyl, or glycosidic linkage.

29. A method according to claim 28, wherein $R_5$ represents a methyl group, $R_6$ represents an ethyl group, and $R_7$ represents a hydroxyl group.

30. A method according to claim 28, wherein $R_5$, $R_6$, and $R_7$ each represent hydrogen.

31. A method according to claim 26, wherein Y represents a hydroxyl group.

32. A method according to claim 26, wherein Y represents hydrogen.

33. A method according to claim 26 wherein Y comprises an ester sidechain represented by the formula

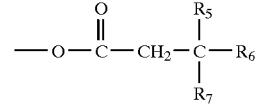

wherein $R_5$, $R_6$, and $R_7$ represent hydrogen, halogen, methyl, ethyl, alkyl, aryl, hydroxyl, carboxyl, glycine, glycosaccharides, water soluble sidechains, amino acid, peptide, polypeptide, protein, and any of the foregoing attached to the central carbon by an ether, ester, carbonyl, or glycosidic linkage.

34. A method according to claim 33, wherein $R_5$ represents an ethyl group, $R_6$ represents an ethyl group, and $R_7$ represents a hydroxyl group.

35. A method for treating solid tumors comprising the steps of preparing a pharmaceutically active composition containing a quassinoid represented by the formula

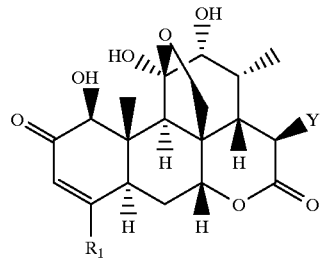

wherein $R_1$ represents hydrogen, oxygen, alkyl, alkenyl, acyl, aryl, halogen, sulfo, nitro, carboxyl, hydroxyl, hydroxyalkyl, alkoxy, or other water soluble sidechain, and Y is a sidechain comprising hydrogen, alkyl, hydroxyalkyl, carboxyl, aryl, alkenyl, cycloalkanes, cycloalkenes, glycine, glycosaccharides, water soluble sidechains selected from the group consisting of:

dextrans, dextrins, cyclodextrins, polyethyleneglycols, polymers of ethyleneglycol, polymers of propyleneglycol, carbohydrate polymers, carboxymethylcellulose, polyamines, polyglutamine, N-(2-hydroxypropyl)methacrylamide copolymers, polyoxamines, polyoxyethylene block polymers, and polyoxypropylene block polymers, amino acid, peptide, polypeptide, lipids, nucleic acids derivatized polymeric substances, naturally occurring macromolecules, protein selected from the group consisting of:

antibodies, immunoglobulins, growth hormones, interferons, plasma albumin, plasminogen activator, soybean trypsin inhibitor, L-asparaginase, and ribonuclease, and any of the foregoing attached to the C-15 carbon by an ether, ester, carbonyl, or glycosidic linkage, with the proviso that said quassinoid is not ailanthinone, glaucarubinone, chaparrinone, glaucarubolone, castelanone, soularubinone, holacanthone, glaucarubolone-15-benzoate, 2'-acetylglaucarubinone, or glaucarubolone-15-tiglate, and with the further proviso that said Y is not a $C_5$ to $C_{18}$ 2-alkenoate or a $C_5$ to $C_{16}$ 3-methylalkenoate, and contacting the solid tumors with said pharmaceutically active composition.

36. A compound characterized by the formula

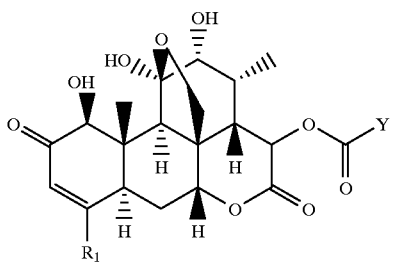

wherein $R_1$ represents hydrogen, oxygen, an alkyl having at least two carbons, alkenyl, acyl, aryl, halogen, sulfo, nitro, carboxyl, hydroxyl, hydroxyalkyl, alkoxy, or other water soluble sidechain, and Y is a sidechain comprising hydrogen, alkyl, hydroxyalkyl, carboxyl, aryl, alkenyl, cycloalkanes, cycloalkenes, glycosaccharides, water soluble sidechains, polymers, amino acid, peptide, polypeptide, protein, and any of the foregoing attached by an ether, ester, carbonyl, or glycosidic linkage, with the proviso that said quassinoid is not ailanthinone, glaucarubinone, chaparrinone, glaucarubolone, castelanone, soularubinone, holacanthone, glaucarubolone-15-benzoate, 2'-acetylglaucarubinone, or glaucarubolone-15tiglate, and with the further proviso that said Y is not a $C_5$ to $C_{18}$ 2-alkenoate or a $C_5$ to $C_{16}$ 3-methylalkenoate.

37. The compound of claim 36 wherein Y includes a water soluble sidechain selected from the group consisting of:

dextrans, dextrins, cyclodextrins, polyethyleneglycols, polymers of ethyleneglycol, polymers of propyleneglycol, carbohydrate polymers, carboxymethylcellulose, polyamines, polyglutamine, N-(2-hydroxypropyl)methacrylamide copolymers, polyoxamines, polyoxyethylene block polymers, and polyoxypropylene block polymers.

38. A compound characterized by the formula

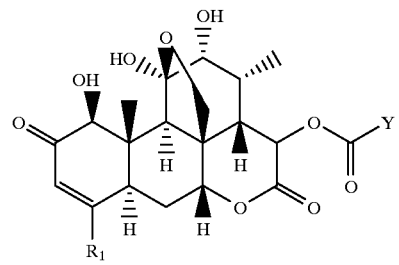

wherein $R_1$ represents hydrogen, oxygen, alkyl, alkenyl, acyl, aryl, halogen, sulfo, nitro, carboxyl, hydroxyl, hydroxyalkyl, alkoxy, or water soluble sidechain, and Y is a sidechain comprising hydrogen, carboxyl, aryl, cycloalkanes, cycloalkenes, glycosaccharides, water soluble sidechains, amino acid, polymers, peptide, polypeptide, protein, lipids, nucleic acids, derivatized polymeric substances, naturally occurring macromolecules, and any of the foregoing attached by an ether, ester, carbonyl, or glycosidic linkage, with the proviso that said quassinoid is not ailanthinone, glaucarubinone, chaparrinone, glaucarubolone, castelanone, soularubinone, holacanthone, glaucarubolone-15-benzoate, 2'-acetylglaucarubinone, or glaucarubolone-15-tiglate, and with the further proviso that said Y is not a $C_5$ to $C_{18}$ 2-alkenoate or a $C_5$ to $C_{16}$ 3-methylalkenoate.

39. The compound of claim 38 wherein Y includes a water soluble sidechain selected from the group consisting of:

dextrans, dextrins, cyclodextrins, polyethyleneglycols, polymers of ethyleneglycol, polymers of propyleneglycol, carbohydrate polymers, carboxymethylcellulose, polyamines, polyglutamine, N-(2-hydroxypropyl) methacrylamide copolymers, polyoxamines, polyoxyethylene block polymers, and polyoxypropylene block polymers.

40. The compound of claim 38 wherein Y includes a naturally occurring molecule selected from the group consisting of:

immunoglobulins, growth hormones, insulin, interferons, plasma albumin, fibrinogen, plasminogen activator, heparin, chondroitin sulfate, soybean trypsin inhibitor, L-asparaginase, and ribonuclease.

41. The method of claim 4, wherein Y comprises a water soluble sidechain selected from the group consisting of:

dextrans, dextrins, cyclodextrins, polyethyleneglycols, polymers of ethyleneglycol, polymers of propyleneglycol, carbohydrate polymers, carboxymethylcellulose, polyamines, polyglutamine, N-(2-hydroxypropyl)methacrylamide copolymers, polyoxamines, polyoxyethylene block polymers, and polyoxypropylene block polymers.

42. The method of claim 6, wherein Y comprises a water soluble sidechain selected from the group consisting of:

dextrans, dextrins, cyclodextrins, polyethyleneglycols, polymers of ethyleneglycol, polymers of propyleneglycol, carbohydrate polymers, carboxymethylcellulose, polyamines, polyglutamine, N-(2-hydroxypropyl)methacrylamide copolymers, polyoxamines, polyoxyethylene block polymers, and polyoxypropylene block polymers.

* * * * *